(12) United States Patent
Donoghue et al.

(10) Patent No.: US 7,392,079 B2
(45) Date of Patent: Jun. 24, 2008

(54) NEUROLOGICAL SIGNAL DECODING

(75) Inventors: John Philip Donoghue, Providence, RI (US); Nicholas George Hatsopoulos, Chicago, IL (US); Mijail Demian Serruya, Providence, RI (US); Matthew Richard Fellows, Providence, RI (US); Liam Paninski, Astoria, NY (US)

(73) Assignee: Brown University Research Foundation, Providence, RI (US)

( * ) Notice: Subject to any disclaimer, the term of this patent is extended or adjusted under 35 U.S.C. 154(b) by 102 days.

(21) Appl. No.: 11/376,122

(22) Filed: Mar. 16, 2006

(65) Prior Publication Data
US 2007/0046486 A1 Mar. 1, 2007

Related U.S. Application Data

(63) Continuation of application No. 09/991,498, filed on Nov. 14, 2001, now abandoned.

(51) Int. Cl.
*A61B 5/04* (2006.01)
(52) U.S. Cl. ...................................... 600/545
(58) Field of Classification Search ................ 600/545, 600/26, 595; 607/49; 463/36
See application file for complete search history.

(56) References Cited

U.S. PATENT DOCUMENTS

| | | | |
|---|---|---|---|
| 3,837,339 A | 9/1974 | Aisenberg et al. |
| 3,850,161 A | 11/1974 | Liss |
| 4,055,175 A | 10/1977 | Clemens et al. |
| 4,146,029 A | 3/1979 | Ellinwood, Jr. |
| 4,294,245 A | 10/1981 | Bussey |
| 4,360,031 A | 11/1982 | White |
| 4,461,304 A | 7/1984 | Kuperstein |
| 4,633,889 A | 1/1987 | Talalla et al. |
| 4,690,142 A | 9/1987 | Ross et al. |
| 4,837,049 A | 6/1989 | Byers et al. |
| 4,865,048 A | 9/1989 | Eckerson |
| 4,878,913 A | 11/1989 | Aebischer et al. |
| 4,883,666 A | 11/1989 | Sabel et al. |

(Continued)

FOREIGN PATENT DOCUMENTS

WO    WO 01/43635    6/2001

(Continued)

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

(Continued)

*Primary Examiner*—Max Hindenburg
*Assistant Examiner*—Fangemonique Smith
(74) *Attorney, Agent, or Firm*—Finnegan, Henderson, Farabow, Garrett & Dunner, L.L.P.

(57) ABSTRACT

A system using neurological control signals to control a device is disclosed. The system may include a sensor sensing electrical activity of a plurality of neurons over time and a vector generator generating a neural control vector from the sensed electrical activity of the plurality of neurons over time. The system may also include a control filter to which the neural control vector is applied to provide a control variable and an output device controlled by the control variable.

12 Claims, 18 Drawing Sheets

U.S. PATENT DOCUMENTS

| | | | |
|---|---|---|---|
| 4,969,468 A | 11/1990 | Byers et al. | |
| 5,037,376 A | 8/1991 | Richmond et al. | |
| 5,081,990 A | 1/1992 | Deletis | |
| 5,119,832 A | 6/1992 | Xavier | |
| 5,156,844 A | 10/1992 | Aebischer et al. | |
| 5,215,088 A | 6/1993 | Normann et al. | |
| 5,325,865 A | 7/1994 | Beckman et al. | |
| 5,361,760 A | 11/1994 | Normann et al. | |
| 5,423,877 A | 6/1995 | Mackey | |
| 5,445,608 A | 8/1995 | Chen et al. | |
| 5,458,631 A | 10/1995 | Xavier | |
| 5,474,547 A | 12/1995 | Aebischer et al. | |
| 5,617,871 A | 4/1997 | Burrows | |
| 5,638,826 A | 6/1997 | Wolpaw et al. | |
| 5,687,291 A | 11/1997 | Smyth | |
| 5,692,517 A | 12/1997 | Junker | |
| 5,697,951 A | 12/1997 | Harpstead et al. | |
| 5,702,432 A | 12/1997 | Chen et al. | |
| 5,713,923 A | 2/1998 | Ward et al. | |
| 5,735,885 A | 4/1998 | Howard, III et al. | |
| 5,758,651 A | 6/1998 | Nygard et al. | |
| 5,797,898 A | 8/1998 | Santini, Jr. et al. | |
| 5,814,089 A | 9/1998 | Stokes et al. | |
| 5,843,093 A | 12/1998 | Howard, III | |
| 5,843,142 A | 12/1998 | Sultan | |
| 5,855,801 A | 1/1999 | Lin et al. | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 6,001,065 A * | 12/1999 | DeVito | 600/544 |
| 6,006,124 A | 12/1999 | Fischell et al. | |
| 6,016,449 A | 1/2000 | Fischell et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,061,593 A | 5/2000 | Fischell et al. | |
| 6,086,582 A | 7/2000 | Altman et al. | |
| 6,091,015 A | 7/2000 | del Valle et al. | |
| 6,092,058 A | 7/2000 | Smyth | |
| 6,094,598 A | 7/2000 | Elsberry et al. | |
| 6,113,553 A | 9/2000 | Chubbuck | |
| 6,125,300 A | 9/2000 | Weijand et al. | |
| 6,128,527 A * | 10/2000 | Howard et al. | 600/544 |
| 6,128,538 A | 10/2000 | Fischell et al. | |
| 6,134,474 A | 10/2000 | Fischell et al. | |
| 6,154,678 A | 11/2000 | Lauro | |
| 6,161,045 A | 12/2000 | Fischell et al. | |
| 6,163,725 A | 12/2000 | Peckham et al. | |
| 6,169,981 B1 | 1/2001 | Werbos | |
| 6,171,239 B1 | 1/2001 | Humphrey | |
| 6,175,762 B1 | 1/2001 | Kirkup et al. | |
| 6,181,965 B1 | 1/2001 | Loeb et al. | |
| 6,185,455 B1 | 2/2001 | Loeb et al. | |
| 6,216,045 B1 | 4/2001 | Black et al. | |
| 6,224,549 B1 | 5/2001 | Drongelen | |
| 6,240,315 B1 | 5/2001 | Mo et al. | |
| 6,254,536 B1 | 7/2001 | DeVito | |
| 6,263,237 B1 | 7/2001 | Rise | |
| 6,280,394 B1 | 8/2001 | Maloney et al. | |
| 6,309,410 B1 | 10/2001 | Kuzma et al. | |
| 6,313,093 B1 | 11/2001 | Frey, II | |
| 6,319,241 B1 | 11/2001 | King et al. | |
| 6,353,754 B1 | 3/2002 | Fischell et al. | |
| 6,354,299 B1 | 3/2002 | Fischell et al. | |
| 6,356,784 B1 | 3/2002 | Lozano et al. | |
| 6,358,202 B1 | 3/2002 | Arent | |
| 6,360,122 B1 | 3/2002 | Fischell et al. | |
| 6,366,813 B1 | 4/2002 | Di Lorenzo | |
| 6,427,086 B1 | 7/2002 | Fischell et al. | |
| 6,436,708 B1 | 8/2002 | Leone et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,577,893 B1 | 6/2003 | Besson et al. | |
| 6,620,415 B2 | 9/2003 | Donovan | |
| 2001/0023368 A1 | 9/2001 | Black et al. | |
| 2001/0027336 A1 | 10/2001 | Gielen et al. | |
| 2001/0029391 A1 | 10/2001 | Gluckman et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0013612 A1 | 1/2002 | Whitehurst | |
| 2002/0016638 A1 | 2/2002 | Mitra et al. | |
| 2002/0077620 A1 | 6/2002 | Sweeney et al. | |
| 2002/0099412 A1 | 7/2002 | Fischell et al. | |
| 2002/0169485 A1 | 11/2002 | Pless et al. | |
| 2003/0004428 A1 | 1/2003 | Pless et al. | |
| 2003/0082507 A1 | 5/2003 | Stypulkowski | |
| 2003/0083716 A1 | 5/2003 | Nicolelis et al. | |
| 2003/0083724 A1 | 5/2003 | Jog et al. | |
| 2003/0093129 A1 | 5/2003 | Nicolelis et al. | |

FOREIGN PATENT DOCUMENTS

| | | |
|---|---|---|
| WO | WO 01/60445 | 8/2001 |
| WO | WO 01/93756 A2 | 12/2001 |
| WO | WO 02/093312 A2 | 11/2002 |
| WO | WO 02/100267 A1 | 12/2002 |
| WO | WO 03/035165 | 5/2003 |
| WO | WO 03/037231 | 5/2003 |
| WO | WO 03/061465 | 7/2003 |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minnesota Epilepsy Group of United and St. Paul Children's Hospital; and Human Motor Control Section, National Institute of Neurological Disorders and Stroke, National Institutes of Health, Electroencephalorophy and Clinical Neurophysiology, No. 93, 1994, pp. 390-403.
Anthony L. Owens et al., "Multi-electrode array for measuring evoked potentials from surface of ferret primary auditory cortex," Journal of Neuroscience Methods, vol. 58, Nos. ½, May 1995, pp. 209-220.
Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.
Jerome N. Sanes et al., "Shared Neural Substrates Controlling Hand Movements in Human Motor Cortex," Science, vol. 268, Jun. 23, 1995, pp. 1775-1777.
D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. ⅔, 1995, pp. 237-278.
Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.
Apostolos P. Georgopoulos et al., "Neuronal Population Coding of Movement Direction," Science, vol. 233, Sep. 26, 1986, pp. 1416-1419.
Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.
Patrick K. Campbell et al., "A chronic intracortical electrode array: Preliminary results," Journal of Biomed. Material Res.: Applied Biomaterials, vol. 23, No. 2, 1989, pp. 245-259.
Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.
Patrick K. Campbell et al., "A Silicon-Based, Three-Dimensional Neural Interface: Manufacturing Processes for an Intracortical Electrode Array," IEEE Transactions, 1991, pp. 758-768.
A. C. Hoogerwerf et al., "A Three-Dimensional Neural Recording Array," IEEE Transactions, 1991, pp. 120-123.
Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.
Kelly E. Jones et al., "A Glass/Silicon Composite Intracortical Electrode Array," Annals of Biomedical Engineering. vol. 20, 1992, pp. 423-437.
Miquel A. L. Nicolelis et al., "Induction of immediate spatiotemporal changes in thalamic networks by peripheral block of ascending cutaneous information," Letters to Nature, vol. 361, Feb. 11, 1993, pp. 533-536.
Reinhard Eckhorn et al., "A new method for the insertion of multiple microprobes into neural and muscular tissue, including fiber electrodes, fine wires, needles and microsensors," Journal of Neruroscience Methods, vol. 49, Nos. ½, 1993, pp. 175-179.
Craig T. Nordhausen et al., "Optimizing recording capabilities of the Utah Intracortical Electrode Array," Brain Research, vol. 637, Nos. ½, Feb. 21, 1994, pp. 27-36.
Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.
Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.
Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.
Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.
P. Nisbet, "intergrating assistive technologies: current practices and future possibilities," Med. Eng. Phys., vol. 18, No. 3, 1996, pp. 193-202.
Miguel A. L. Nicolelis et al., "Reconstructing the Engram: Simultaneous, Multisite, Many Sinle Neuron Recordings," Nueron, vol. 18, Apr. 1997, pp. 529-537.
TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.
Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.
Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.
Robert M. Bradley et al., "Long term chronic recordings from peripheral sensory fibers using a sieve electrode array," Journal of Neuroscience Methods, vol. 73, 1997, pp. 177-186.
David K. Warland et al., "Decoding Visual Information From a Population of Retinal Ganglion Cells," The American Physiological Society, 1997, pp. 2336-2350.
Steven P. Wise et al., "Premotor and Parietal Cortex: Cortiococortical Connectivity and Combinatorial Computations," Annual Review of Neuroscience, vol. 20, 1997, pp. 25-42.
P.R. Kennedy et al., "Restoration of neural output from a paralyzed patient by a direct brain connection," NeuroReport, vol. 9, No. 8, Jun. 1998 pp. 1707-1711.
Paolo Dario et al., "Neural Interfaces for Regenerated Nerve Stimulation and Recording," IEEE Transactions on Rehabilitation Engineering, vol. 6, No. 4, Dec. 1998, pp. 353-363.
Nicholas G. Hatsopoulos et al., "Information about movement direction obtained from synchronous activity of motor cortical neurons," Proc. Natl. Acad. Sci. USA, vol. 95, Dec. 19, 1998, pp. 15706-15711.
John P. Donoghue et al., "Neural Discharge and Local Field Potential Oscillations in Primate Motor Cortex During Voluntary Movements," The American Physiological Society, 1998, pp. 159-173.
Nicolellis, Miguel A.L., "Trigeminal System Plasticity During Facial Anethesia," Department of Health and Human Services, Public Health Service, Grant No. 2 R01 DE11451-06, Apr. 1999.
Gregor Rainer et al., "Prospective Coding for Objects in Primate Prefrontal Cortex," The Journal of Neuroscience, vol. 19, No. 13, Jul. 1, 1999, pp. 5493-5505.
John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.
E. M. Maynard et al, "Neuronal Interactions Improve Cortical Population Coding of Movement Direction," The journal of Neuroscience, vol. 19, No. 18, Sep. 15, 1999, pp. 8083-8093.
F. Gandolfo et al., "Cortical correlates of learning in monkeys adapting to a new dynamical environment," PNAS, vol. 97, No. 5, Feb. 29, 2000, pp. 2259-2263.
J. F. Marsden et al., "Organization of Cortical Activities Related to Movement in humans," The Journal of Neuroscience, vol. 20, No. 6, Mar. 15, 2000, pp. 2307-2314.
D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.
Qing Bai et al., "A HIgh-Yield Microassembly Structure For Three-Dimensional Microelectrode Arrays," IEEE Transactions on Biomedical Engineering, vol. 47, No. 3, Mar. 2000, pp. 281-289.
Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real-Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patric J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigerminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University: and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6,8 and 9 pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Services, National Institute of Dental and Craniofacial Research of the Nationsl Institutes of Health, Grant No. 5 R01 DE013810-02, Mar. 2002.

Nicolelis, Migueal A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter,"Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

Norretranders, Tor, "The User Illusion," Penguin Books, 1991, Chapter 12, pp. 310-328.

Mohammad Mojarradi, "A Miniaturized Neuroprosthesis Suitable for Implantation Into the Brain," IEEE Transactions on Neural Systems and Rehabilitation Engineering, vol. 11. No. 1. Mar. 2003.

Mortein K. Haugland et al., "Cutaneous Whole Nerve Recordings Used for Correction of Fooldrop in Hemiplegic Man," IEEE Transactions on Neural Systems and Rehabilitation Engineering, vol. 3, No. 4, Dec. 1995.

Paninski et al., "Coding Dynamic Variables in Puopulations of Motor Cortex Neurons," Society for Neuroscience, 29th Annual Meeting, Miami Beach, FL, Oct. 23-28, 1999, Abstract at vol. 25, p. 1663, and Poster.

Van Nest et al., "Population Discharge Patterns of Motor Cortical Cells Change More with Motor Learning than with Performance of an Overlearned Task," Society for Neuroscience, 30th Annual Meeting, New Orleans, LA, Nov. 4-9, 2000, Abstract at vol. 26, p. 680.

Serruya et al., "Assignment of Primate MI Cortical Activity to Robot Arm Position with Bayesian Reconstruction Algorithm," Society for Neuroscience, 30th Annual Meeting, New Orleans, LA, Nov. 4-9, 2000, Abstract at vol. 26, p. 1227.

Hatsopoulos et al., "Assessing Precise Temporal Patterns of Spikes Among Cortical Neurons," Society for Neuroscience, 31st Annual Meeting, San Diego, CA, Nov. 10-15, 2001, Abstract No. 63.1, vol. 27, vol. 27.

Fellows et al., "Diverse Spatial and Temporal Features of Velocity and Position Turning in MI Neurons During Continuous Tracking," Society for Neuroscience, 31st Annual Meeting, San Diego, CA, Nov. 10-15, 2001, Abstract No. 940.1, vol. 27, and Poster.

Serruya et al., "Algorithms for Realtime Control of a Motor Neuroprosthetic Device," Society for Neuroscience, 31st Annual Meeting, San Diego, CA, Nov. 10-15, 2001, Abstract No. 302.13, vol. 27.

Gao et al., "Encoding/Decoding of Arm Kinematics from Simultaneously Recorded MI Neurons," Society for Neuroscience, 31st Annual Meeting, San Diego, CA, Nov. 10-15, 2001, Abstract.

Shoham et al., "New Method for Nonlinear Decoding of Multiple Neural Spike Trains," Society for Neuroscience, 31st Annual Meeting, San Diego, CA, Nov. 10-15, 2001, Abstract No. 808.7, vol. 27.

Marcia Barinaga, "Turning Thoughts Into Actions," Science, vol. 286, Oct. 29, 1999, pp. 888-890.

Philip L. Newland et al., "Dynamics of Neurons Controlling Movements of a Locust Hind Leg-11. Flexor Tibiae Motor Neurons," Journal of Neurophysiology, vol. 77, No. 4, Apr. 1997, pp. 1731-1746.

John K. Chapin et al., Neural Prostheses for Restoration of Sensory and Motor Function, "Chapter 8—Brain Control of Sensorimotor Prostheses," pp. 235-261.

D.M. Taylor et al., "Using Virtual Reality to Modify Motor Cortex Activity to Convey More Movement Information for Better Control of a Neural Prosthesis," Society for Neuroscience, 30th Annual Meeting, New Orleans, LA, Nov. 4-9, 2000, vol. 26, Part 1, Abstract No. 458.1.

S.I. Helms Tillery et al., "Online Control of a Prosthetic Arm from Motor Cortical Signals," Society for Neuroscience, 30th Annual Meeting, New Orleans, LA, Nov. 4-9, 2000, vol. 26, Part 1, Abstract. No. 458.2.

J. Wessberg et al., "Prediction of Hand Position by Neuronal Ensembles in Primate Motor, Premotor, and Parietal Cortex During an Arm-Movement Task," Society for Neuroscience, 30th Annual Meeting, New Orleans, LA, Nov. 4-9, 2000, vol. 26, Part 1, Abstract No. 458.4.

J.D. Kralik et al., "Chronic Cortical Ensemble Recordings From Primate Cortex During Performance of a Free Arm Reaching Task," Society for Neuroscience, 30th Annual Meeting, New Orleans, LA, Nov. 4-9, 2000, vol. 26, Part 1, Abstract No. 458.5.

M. Laubach et al., "Functional Interactions Between Primary Motor, Dorsal Premotor and Posterior Parletal Cortices During Arm Movements," Society for Neuroscience, 30th Annual Meeting, New Orleans, LA, Nov. 4-9, 2000, vol. 26, Part 1, Abstract No. 458.6.

P.P. Mitra et al., "A Robust, Unified Framework for Decoding Temporal Structure in Neuronal Activity with Applications to Neuromotor Prosthetics," Society for Neuroscience, 30th Annual Meeting, New Orleans, LA, Nov. 4-9, 2000, vol. 26, Part 1, Abstract No. 449.7.

D.J. Dubowitz et al., "A Frameless Stereotaxic MRI Technique for Placing Neural Recording Electrodes," Society for Neuroscience, 30th Annual Meeting, New Orleans, LA, Nov. 4-9, 2000, vol. 26, Part 1, Abstract No. 828.12.

D.R. Humphrey et al., "Voluntary Activation of Ineffective Cerebral Motor Areas in Short- and Long-Term Paraplegics," Society for Neuroscience, 30th Annual Meeting, New Orleans, LA, Nov. 4-9, 2000, vol. 26, Part 1, Abstract No. 253.3.

S.I. Helms Tillery et al., "Training Non-Human Primates to Use a Neuroprosthetic Device" Society for Neuroscience, 31th Annual Meeting, San Diego, CA, Nov. 10-15, 2001, vol. 27, Part 1, Abstract No. 63.4

P.R. Kennedy et al., "Motor Cortical Control of a Cyber Digit by a Patient Implanted with the Neurotrophic Electrode," Society for Neuroscience, 31st Annual Meeting, San Diego, CA, Nov. 10-15, 2001, vol. 27, Part 1, Abstract No. 63.5.

D. Meeker et al., "Cognitive Control Signals for Prosthetic Systems," Society for Neuroscience, 31st Annual Meeting, San Diego, CA, Nov. 10-15, 2001, vol. 27, Part 1, Abstract No. 63.6.

J. Wesseberg et al., "Algorithms for Sensory Feedback and Real-Time Control of a Robotic Device Based on Cortical Ensemble Recordings from Primate Cortex," Society for Neuroscience, 31st Annual Meeting, San Diego, CA, Nov. 10-15, 2001, vol. 27, Part 1, Abstract No. 63.9.

H. Sheikh et al., "EEG-Based Brain-Computer Interface (BCI) Communication: Comparison of Alternative Signal Processing Methods for Time-Domain EEG Activity," 31st Annual Meeting, San Diego, CA, Nov. 10-15, 2001, vol. 27, Part 1, Abstract No. 63.18.

G. Schalk et al., "BCI2000: Development of a General Purpose Brain-Computer Interface (BCI) System," Society for Neuroscience, 31st Annual Meeting, San Diego, CA, Nov. 10-15, 2001, vol. 27, Part 1, Abstract No. 63.19.

D.M. Taylor et al., "Direct 3D Control of an upper Limb Neural Prosthesis Using Motor Cortex Cells Trained in a Brain-Controlled Virtual Movement Task," Society for Neuroscience, 31st Annual Meeting, San Diego, CA, Nov. 10-15, 2001, vol. 27, Part 1, Abstract No. 129.6.

B. Pesaran et al., "Spectral Measures and Statistical Models of the Temporal Structure in Neuronal Spike Trains," Society for Neuroscience, 31st Annual Meeting, San Diego, CA, Nov. 10-15, 2001, vol. 27, Part 2, Abstract No. 821.39.

* cited by examiner

NEUROLOGICAL SIGNAL DECODING

This is a continuation of application Ser. No. 09/991,498, filed Nov. 14, 2001, now abandoned which is incorporated herein by reference.

GOVERNMENT SUPPORT

The invention was supported, in whole or in part, by a grant NINDS NS25074, NINDS contract NS9-2322 from NIH and DARPA grant number MDA 972-00-1-0026. The Government has certain rights in the invention.

BACKGROUND OF THE INVENTION

Primates are particularly adept at directing their hand to a visual target, even when the target is moving in an uncertain way. Visually guided movement is fundamental to many behaviors, but the nature of cortical coding of this behavior is not understood. The process of using vision for manual tracking engages a collection of cortical areas. Primary motor cortex (Ml) is one important area near the final stages of hand motion control. Single neuron recordings in behaving animals have demonstrated that information about movement direction, velocity, speed, position and acceleration, as well as force can be obtained from the firing rate of single Ml neurons (e.g., see Ashe and Georgopoulos, 1994), suggesting that each of these movement features may be coded in Ml. However, understanding what and how information about hand motion is coded in Ml has been difficult to determine. Firing rates of individual neurons may combine information about multiple kinematic features (Ashe, J. & Georgopoulos, A. Movement parameters and neural activity in motor cortex and area 5. Cerebral Cortex 4, 590-600. 1994) that may be specified separately in time (Fu, Q. G., Flament, D., Coltz, J. D. & Ebner, T. J. Temporal encoding of movement kinematics in the discharge of primate primary motor and premotor neurons. Journal of Neurophysiology 73, 836-854 1995). Attempts at decoding the information carried in Ml neurons has shown that averaging firing of groups of neurons provides a reasonable estimate of some of these parameters, particularly the direction of intended hand movement, further supporting the view that these features are processed in Ml.

One major difficulty in understanding coding of hand motion in MI is relating behavior to neural activity. Most prior studies treat motor variables not as time-varying signals, but as static quantities. The properties of neurons are often summarized from the average direction of hand motion or the static, over learned location of movement targets, rather than a time varying code for hand motion that is being continuously guided directly by vision. Static tasks present a number of difficulties in addressing the combined spatial and temporal aspects encoded by Ml neurons. First, the amount of space sampled for each variable is limited. Studies of direction coding are typically limited to a small subset of possible target directions (eight, in the widely used 'center-out task'). A second problem with such tasks is that there is limited control over variables—how a hand moves between targets is a function of the animal's strategy, not the experiment's design. Consequently various statistical dependencies can appear in hand motion, including position and velocity and movement speed and initiation. Further, firing rate (which are usually actively sought for their high modulation rate) is often correlated with these multiple variables. Third, highly parametric models of firing are assumed. Typically, firing rates are reduced to a cosine function, thereby removing more complex structure that may be present in a neuron's firing pattern (Sanger T D. Probability density estimation for the interpretation of neural population codes. J Neurophysiol. October ; 764 :2790-3. 1996). Fourth, these tasks introduce non-stationarities in which neural and behavioral signals co-vary in association with various trial based epochs, making it difficult or incorrect to evaluate motion quantitatively. For example, neurons may have fundamentally different firing regimes during hold and movement periods so that it is difficult to dissociate changes in the apparent relationship between neurons and motor variables from epoch-related aspects of neural encoding (Fu et al., 1995; Maynard, E. M., Hatsopoulos, N. G., Ojakangas, C. L., Acuna, B. D., Sanes, J. N., Normann, R. A. & Donoghue, J. P. Neuronal interactions improve cortical population coding of movement direction. Journal of Neuroscience 19, 8083-809. 1999; Georgopoulos, A. P., Lurito, J. T., Petrides, M., Schwartz, A. B. & Massey, J. T. Mental rotation of the neuronal populaiton vector. Science 243, 234-236 1989). Fifth, it is difficult to compare the detailed features of neural encoding because neurons are recorded serially under behavior, neural or state conditions which may vary for each neuron.

SUMMARY OF THE INVENTION

The present study adopts a new approach to characterize Ml encoding of hand motion. It describes the position and velocity information available in Ml using a systems analysis framework in which we view hand motion as a stimulus and neural activity as the system's response. Continuous tracking provides means to apply this approach. A task was devised in which a randomly moving visual stimulus is continuously tracked by the hand. A novel multielectrode array was used to acquire the activity of multiple Ml neurons simultaneously during this behavior. The stimulus is structured so that its trajectory on each trial is drawn from an experimenter-determined distribution that broadly covers velocity and position space. This design effectively controls hand motion at all times and reduces or removes statistical dependencies among variables across the experiment. The derived relationship between kinematics and firing makes no assumptions about underlying model of firing. In its ideal form, the approach returns an accurate description of the spatial tuning of Ml neurons and also reveals how this tuning evolves over time. The stationarity of the data permits the valid application of information theory so that a neuron's position and velocity information can be quantified and directly compared. Further, cell comparisons of spatiotemporal tuning functions and position and velocity information are possible because multiple neurons are recorded under identical conditions using multielectrode arrays. This approach permits a direct test for the existence of hand trajectory information using signal reconstruction methods. In this study, the spatiotemporal tuning of velocity and position for Ml neurons are described and the information coded within single cells are compared across the population. it is further shown that Ml neurons contain sufficient position and velocity information to reconstruct any new hand trajectory based on information available from the firing of a small number of nearby Ml neurons.

A system which uses a neurological control signal to control a device comprises a sensor which senses electrical activity of many neurons over time, a vector generator which generates a neural control vector, a control filter a controller which applies the neural control vector to the control filter to produce a control variable, and an output device controlled by the control variable. The electrical activity may comprise any of the following: action potentials of neurons; subdural electrocortigram signals; electroencephalogram signals; subthreshold potentials of a neuron; and motor control commands. The electrical activity may be recorded by electrodes implanted into the central nervous system or the sensor may be an array of electrical sensing elements.

The error between the motor output device and an intended output may be minimized by: the control filter providing the least mean square error; a nonlinear weighting of the neural control vector; and/or a neural network of layers, each layer having nodes.

The motor output device can be an animal limb, a prosthetic, a part of the human body, a computer input device, a robotic arm, a neuromuscular stimulator system, an electrode array, a wheelchair, a home appliance, a vehicle or system thereof, a telerobot, an external voice synthesizer, a microchip, and/or a biohyprid neural chip.

The electrical activity may be sensed over many time bins. The time bins may number 1 to 1000, or more and may be 1 to 1000 milliseconds in duration. The sensing array may have 1 to 1000 sensing elements.

The application of the control filter to a neural control vector can be an instantation of an innerproduct.

A method for controlling a device comprises sensing electrical activity of neurons over time with a sensor; generating a neural control vector from the sensed electrical activity; providing a control filter; calculating an innerproduct between the control vector and the control filter, resulting in a motor control variable; and controlling an output device with the control variable. The method may comprise all of the variations previously described for the system for controlling a device described above.

In addition, the method may further include a calibration by tracking a stimulus moving through a motor workspace in at least one spatial dimension, the calibration possibly being based on a pseudorandom task. The calibration may also incorporate a user acquiring stationary and moving targets and using a neural control signal with previously generated filters and neural and kinematic data concurrent with the target acquisition to build new filters.

The method may comprise the sensing of any biological electrical activity in an animal body other than the neural activity.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows. The description is presented by way of examples.

Methods—Behavioral Task

Three monkeys (one *Macaca fasicularis* and two *M. mulatta*) were operantly conditioned to track a randomly moving visual target. Each monkey viewed a computer monitor and gripped a two-link, low-friction manipulandum that constrained hand movement to a horizontal plane. Manipulandum position was sampled at 167 Hz, with an accuracy of 0.25 mm on a digitizing tablet (Wacom Technology Corp., Vancouver, Wash.) and recorded to disk. The task required manually tracking a smoothly and randomly moving target. Hand position was continuously reported on the monitor by a ~0.2° circle (0.5 cm radius on the tablet) (See FIG. 2A). At the beginning of each trial, a 0.6° (1.5 cm tablet radius) red tracking target appeared in a random position drawn from a two-dimensional, zero-covariance Gaussian (up to the cutoff imposed by the edge of the screen), with a mean located at the monitor center. Each monkey was required to align the feedback and target cursor within 1.5 seconds (4 seconds for one monkey), otherwise the target reappeared at a new, independently, identically distributed (i.i.d.) position to begin the next trial. A one second hold period followed target acquisition, after which the target began to move in a smooth, but random, fashion. If the monkey maintained the feedback cursor within the target for 8-10 seconds, a juice reward was delivered. Target position (and thus, to first order, hand position) during this period represented an i.i.d. sample from a stationary two-dimensional Gaussian process; the horizontal and vertical components of hand position were effectively given by an independent sum of many sinusoids with random magnitudes and phases. Thus, the stimulus was a unique, randomly generated signal. The power spectrum of this stationary Gaussian process was left as a free parameter and varied systematically between experiments, so that each stimulus path could be considered an i.i.d. sample from a single, large-dimensional, Gaussian distribution. Monkeys also were trained standard "center-out," (See FIG. 1) (Georgopoulos et al., '82, Maynard et al., '99). Monkeys moved from a center target position to one of eight radially positioned targets; targets were randomly interleaved. Targets were presented during a random (1-1.5 s) instructed delay period in which movement direction was specified, but movement was withheld until a go cue was presented.

Data Recordings

Figure 17:
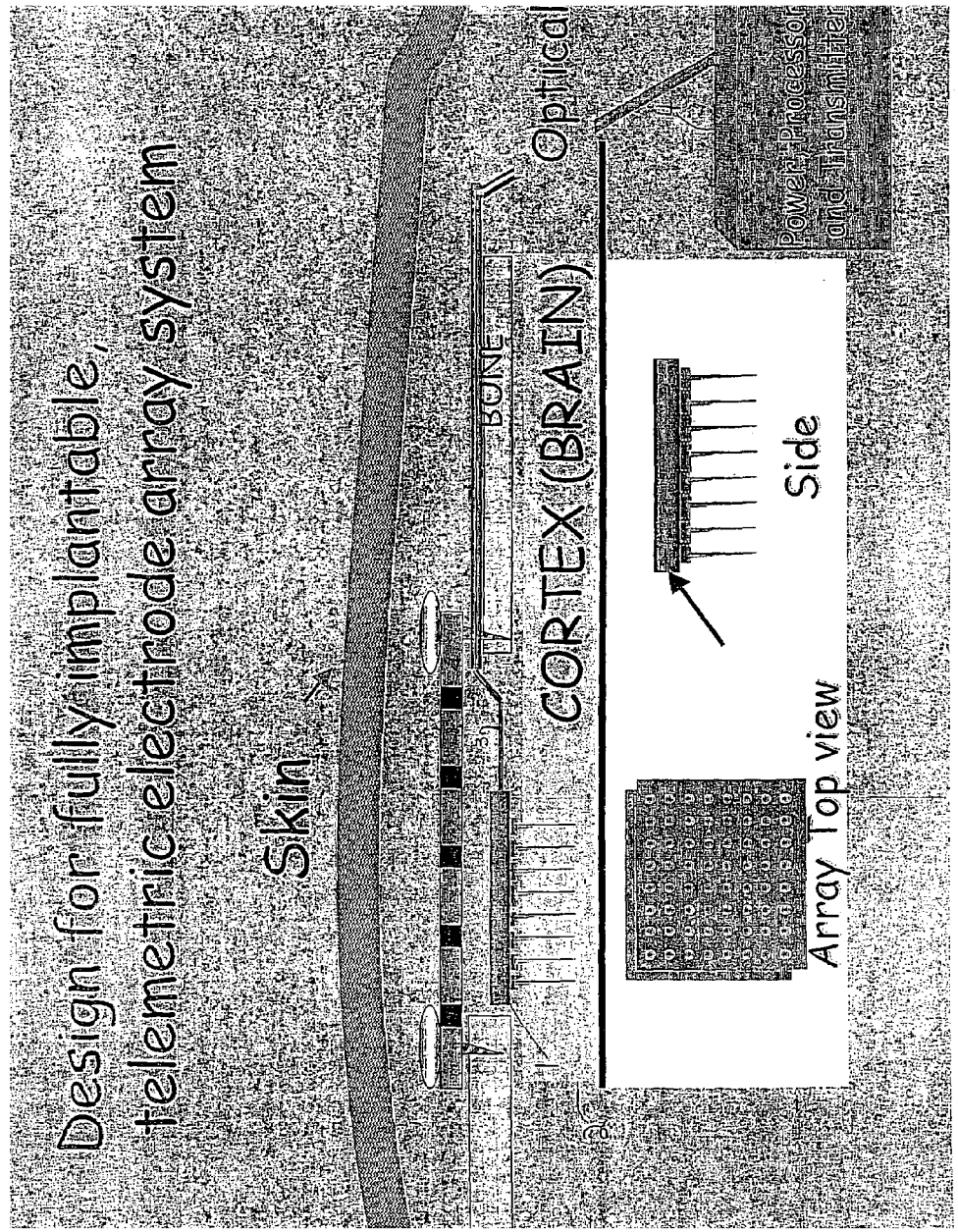
FIG. 17 shows a schematic diagram of a, brain machine interface system.

Details of the basic recording hardware and protocols are available in Donoghue, J. P., Sanes, J. N., Hatsopoulos, N. G. & Gaal, G. Neural discharge and local field potential oscillations in primate motor cortex during voluntary movements. Journal of Neurophysiology 79, 159-173 1998 and Maynard, E. M., Hatsopoulos, N. G., Ojakangas, C. L., Acuna, B. D., Sanes, J. N., Normann, R. A. & Donoghue, J. P. Neuronal interactions improve cortical population coding of movement direction. Journal of Neuroscience 19, 8083-809. 1999. Following task training, a Bionic Technologies LLC (BTL, Salt Lake City, Utah) 100 electrode silicon array was implanted in the arm representation of MI. The array was placed on the pre-central gyrus medial to a line extending from the genu of the arcuate sulcus back to the central sulcus. The BTI arrays consisted of 100 platinized tip silicon probes (200-500 k at 1 kHz; 1 or 1.5 mm in length (Nordhausen, C. T., Maynard, E. M. & Normann, R. A. Single unit recording capabilities of a 100 microelectrode array. Brain Research 726, 129-140 1996), arranged in a square grid (400 μm on center). All procedures were in accordance with Brown University Institutional Animal Care and Use Committee-approved protocols and the Guide for the Care and Use of Laboratory Animals (NIH publication No. 85-23, revised 1985). A diagram of an implantable electrode array system is shown in FIG. 17. The electrode array 1 is inserted into the cortex 2. The array 1 is connected to a cable or wire 3 allowing transmission of the electrical signals sensed by the array 1 to an electronics component 4 of the system. The electronics component 4 of the system may be capable of storing and analyzing the collected data, as well as transmitting data to another part of the system or to an output device.

Signals were amplified and sampled at 30 kHz/channel using a commercial recording system (Bionic Technologies Inc., Salt Lake City, Utah). All waveforms that crossed a manually set threshold were digitized and stored (from 0.33 msec before to 1.17 msec after threshold crossing); spike sorting to isolate single units was performed offline. Single units with signal-to-noise ratios>2.5 were stored as spike times referenced to the stimulus signal for further analysis. Analysis of spiking was confined to data recorded from one second after tracking began to one second before trial end, to eliminate non-stationarities associated with trial beginning and end.

Data Analysis

Spatio-temporal tuning. Spatio-temporal tuning functions were computed to describe firing patterns across kinematic space and across time, with reference to a specific kinematic parameter. These tuning functions are operationally defined as describing the movement space over which the neurons' firing rate is modulated; tuning functions can be considered as a form of receptive field, although the sense of this term in the motor system is not generally established. The functions $N(\vec{p}, \tau)$ and $N(\vec{v}, \tau)$ describe firing for position and velocity, respectively, as a function of time lag. Tuning functions were created at all times $\{t_i\}$ when the hand was moving with a particular velocity (or was located at a particular x,y position) $(\rho \pm d\rho; \theta \pm d\theta)$ cm/sec, for some $\rho$, $\theta$ in polar coordinates. The bin widths (2d $\rho$ and 2d $\theta$) were chosen to be large enough to achieve, on average, >50 samples per bin. Then, the mean firing rates at $\{t_i+\tau\}$ for different time lags, $\tau$, were calculated from the firing rates for each observation of position or velocity. Firing rates at various time lags related to the kinematic reference points are represented by the variable $\tau$, reserving 't' for the time since the beginning of the behavioral trial. Thus, a $\tau$ at lag 100 ms would show the firing rate for a neuron 100 ms before a particular hand velocity occurred. These data were displayed as a series of three dimensional plots, with gray scale coding of the firing rate at each location (either speed and direction, or x and y location). The series represented a set of time slices that plotted firing before (positive lag) and after (negative lag) that kinematic variable.

Data are represented in polar rather than rectangular coordinates for three reasons. First, polar coordinates respect the radial symmetry of the properly scaled, observed Gaussian joint distributions of hand position and velocity (See FIG. 3). In this coordinate frame, all bins at a given radius, $\rho$, are~equiprobable, but this is not true for rectangular coordinates. Second, bin size in polar coordinates ($\rho$, $\theta$) grows with $\rho$, partially correcting for the falloff of the probability distribution of data. Polar coordinates also allows firing rates to be plotted as a function of direction, a convention that facilitates comparisons with prior studies. The origin for tuning functions was taken to be the mean of the distributions of the behavioral variable; in the velocity tuning functions, then, the origin is at (0; 0) cm/sec, while the origin for the position tuning function is at the tablet center.

To summarize the form of tuning functions, the data were fit with sinusoidal or planar functions. The sinusoidal correlation coefficient was measured as $$\rho_{\sin} \equiv \frac{\left|\int_0^{2\pi} (N(\theta)e^{-i\theta})\right|}{\sqrt{(2\pi \int_0^{2\pi} N_0(\theta)^2)}},$$

where |.| denotes complex magnitude and $N_0(\theta)$ is the $\theta$-tuning curve with the baseline firing rate subtracted out (Georgopoulos, A. P., Kalaska, J. F., Caminiti, R. & Massey, J. T. On the relations between the direction of two-dimensional arm movements and cell discharge in primary motor cortex. Journal of Neuroscience 2, 1527-1537 1982). A neuron's preferred direction (PD) is defined by the location of the peak in the $\theta$-tuning curve $N_p(\theta,\tau^1)$ or $N_v(\theta,\tau^1)$, with $\tau^1$ the lag at which the neuron is maximally sinusoidally tuned, i.e., where $\rho_{\sin}$ is maximized. Information-theoretic analysis. The form of the data makes it possible to calculate information provided by neural activity about each variable using information theoretic approaches; the strong advantage of this approach is that information content can be directly compared between variables because this measure is independent of the type of information being carried. The mutual information between any two random signals N and S is defined as (Cover, T. & Thomas, J. Elements of Information Theory. John Wiley & Sons, Inc., New York City, N.Y. 1991)

$$I(N;S) = \int_N p(N) \int_S p(S|N) \log\left(\frac{p(S|N)}{p(S)}\right) \quad (1)$$

where p(.) and P(.|.) denote marginal and conditional probabilities, respectively, and $\int_x$ is the integral over some space X. Information can be an extremely difficult quantity to compute, because full knowledge of the joint distribution p(N;S) (where N and S are functions of time) is needed. This presents a possibly infinite-dimensional learning problem; in the present experiment one would be required to know firing probability at any velocity (or position). Consequently there is no attempt to estimate the information rate between spike trains (denoted N, for neuron) and the behavioral signal (S), rather, information is computed between the observed neuronal firing rate and the behavioral signal (hand velocity or position, here) at discrete (single) time lags, τ, i.e., $$I(N(0); S(\tau)) = \int_{N(0)} p(N(0)) \int_{R^2} p(S(\tau) \mid N(0)) \log\left(\frac{p(S(\tau) \mid N(0))}{p(S(\tau))}\right) \quad (2)$$

The inner integral is taken over $\Re^2$ because the velocity or position at any given time is two-dimensional. N(0) here denotes the activity of the given neuron in the current time bin, and S(τ) denotes the state of the behavioral signal (e.g., the position of the hand) at a time lag r after the present time.

Moreover, empirical observations are used to model the conditional distributions of the behavioral signal given an observed spike count per bin, $p(S(\tau)|N(0)=i)$, $i \in 0,1,2,\ldots$, as Gaussian, with mean $\mu_{\tau,i}$ and covariance matrix $\sigma_{\tau,i}$. Because the prior distributions on S(τ) are near-Gaussian, by construction, they have negligible effect on information calculations. In addition, conditional distributions can validly be modeled as Gaussian, because the mixture of Gaussian distributions with similar means and covariances (the prior expected given Gaussian conditionals) is near-Gaussian. These steps make the information-estimation problem tractable, even with the limited data available here. Thus, instead of equation (2), we calculate $$I(N(0); S(\tau)) = \sum_i p(N(0) = i) \int_{R^2} G(\mu_{\tau,i}, \sigma_{\tau,i}) \log\left(\frac{G(\mu_{\tau,i}, \sigma_{\tau,i})}{\sum (p(N(0) = i)G(\mu_{\tau,i}, \sigma_{\tau,i}))}\right) \quad (3)$$

numerically, where G(μ, σ) is the (2-dimensional) Gaussian density with mean $\mu_{\tau,i}$ and covariance $\sigma_{\tau,i}$. This analysis can be extended to the case where S(0) is replaced by $S=\int_\epsilon d\tau S(\tau)^* f(\tau)$, where f is an arbitrary smooth function, such as a sinusoid or wavelet, and ε is some small positive real number; this allows a simple local frequency analysis. Here we used $\epsilon \approx 2$ seconds and $f_\omega(\tau)=e^{i\omega\tau}$, the usual discrete Fourier basis.

A significance bound was defined as the level above which a significant amount of information was present, as determined by a Monte-Carlo procedure. Under the null hypothesis that the spike trains are a homogeneous Poisson processes, firing rate fluctuations are assumed to be random, have a trivial probabilistic structure, and are independent of the concurrent hand motion. For this analysis, simulated spike trains (homogeneous Poisson processes with rates matched to the observed individual neural firing rates) were generated. Then, mutual information was estimated using these simulated spike trains and real kinematic data (Eq. 3). This procedure produced information values <$10^{-4}$ bits. A different procedure, in which the neural data was shuffled with respect to the behavioral data, so that neural data from one trial was associated, in a random manner, with the behavioral data from a different trial, led to similar results. The significance bound was therefore defined as $I(N(0);S(\tau))>10^{-4}$ (see FIG. 16).

Figure 18:
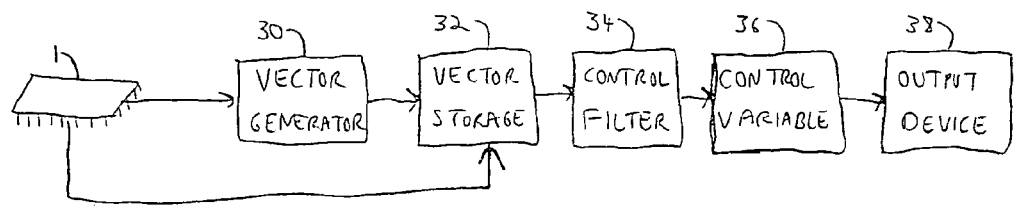
FIG. 18 is a diagram of a signal decoder.
Figure 19:
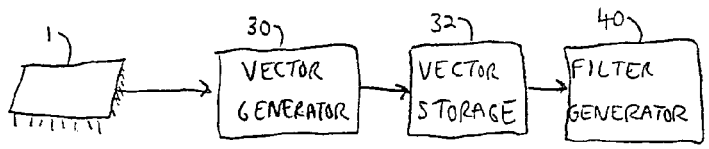
FIG. 19 is a diagram of a filter generator.

Signal reconstruction The ability to reconstruct aspects of hand motion from multiple, simultaneously recorded spike trains was used as a test of availability of position or velocity information in the recorded population. An approach for signal estimation given neural activity was devised, based upon multiple linear regression methods (see Neter, J., Wasserman, W. & Kutner, M. H. Applied linear statistical models. Irwin, Homewood, Ill. (1985); as well as Warland, D., Reinagel, P. & Meister, M. Decoding visual information from a population of retinal ganglion cells. Journal of Neurophysiology 78, 2336-2350 (1997) for time domain applications, and Haag, J. & Borst, A. Active membrane properties and signal encoding in graded potential neurons. Journal of Neuroscience 18 7972-7986 1998 for frequency domain). Referring to FIGS. 18 and 19, after signals are sensed by an array 1, a matrix or vector is generated 30 and stored 32. An estimate or control variable 36, R (for reconstruction), of the position at the current time, t, is given by a linear combination:

$$R(t) = \sum_{i=-(T_{pre})/dt}^{(T_{post})/dt} \sum_{j=1}^{C} a_{i,j} \cdot N(t+i, j) \quad (4)$$

where i indexes time, j the cell number, N(i, j) denotes the activity of cell j at time i (or neural control vector), $a_{i,j}$ the corresponding "weight" or filter coefficient 34, C the number of cells, $T_{pre}$ and $T_{post}$ the time before and after the current time t used to estimate the current position, respectively, and dt the width of the time bins used. R(t) serves as the control variable 36 during signal reconstruction. To calculate filter coefficients $a_{i,j}$ neural spike count and kinematic data k were placed into fixed bins. Linear filters were constructed by building a response matrix containing the firing rate history of each neuron for T seconds, and regressing this matrix onto the two columns of kinematic absolute positions using a psuedo-inverse technique. This comprises a closed-form solution of the least-squares formulation:

$$R(t)=N \cdot a=N(NTN)^{-1}NTk$$

where N is the response matrix, a is the linear filter, k comprises the kinematic values (absolute position), and R is the reconstruction. The response matrix was built in the format outlined by Warland et al. (1997)). Two filters were generated (one each for x(t) and y(t)). The analytical solution to the optimal linear estimation problem in the time domain involves the inversion of a correlation matrix (or vector) that can be fairly large (matrix size=$D^2$, where D=1+C·($T_{pre}$+$T_{post}$)/dt); standard singular value decomposition (Press, W. H., Teukolsky, S. A., Vetterling, W. T. & Flannery, B. P. Numerical Recipes in C. Cambridge University Press, Cambridge, 1992) techniques were used to check the numerical stability of this matrix inversion when D was large. The data showed no evidence of over-fitting such as a decrease in performance as D became large. None of the results shown were smoothed, nor were any relevant parameters subjectively selected (e.g., to select the "best" neurons for analysis). The solution of the linear regression problem is termed the "optimal linear estimator" because it weights terms to provide the optimal fit to the data in an unbiased manner.

Cross validation methods were used to estimate the generality of the linear regression function to decode hand motion from neural population activity. Cross validation tests the ability for a function to reconstruct motion from any subsequent spike train process. Regression functions were created from all but ten trials of a data set. This process was iterated multiple times as successive blocks of a different set of 10 trials were used to test the function. This generated a distribution of reconstruction errors. The measure of error was calculated as, $$r^2 = 1 - \frac{E[(R-S)^2]}{E(S^2)},$$

where R is the reconstructed hand position.

Three types of error measures were used to evaluate the performance of the linear filters: (1) the absolute Euclidean distance (in cm) between the actual and reconstructed positions $$\left(\sum_{i=1}^{n}\sqrt{(x_i - \hat{x}_i)^2 + (y_i - \hat{y})^2}\right),$$

(2) the fraction of the variance of the actual position accounted for by that of the reconstruction $$\left(1 - \frac{\sum_{i=1}^{n}(x_i - \hat{x}_i)^2}{\sum_{i=1}^{n}(x_i - \bar{x})^2}\right),$$

and (3) the correlation coefficient between the actual and reconstructed positions $$\left(\frac{\sum_{i=1}^{n}(x_i - \bar{x}_i)\cdot(\hat{x} - \bar{\hat{x}}_i)}{\sqrt{\left(\sum_{i=1}^{n}(x_i - \bar{x}_i)^2\right)\cdot\left(\sum_{i=1}^{n}(\hat{x} - \bar{\hat{x}})^2\right)}}\right).$$

Separate correlation coefficients and fractions of variance were computed each for the absolute horizontal (x) and vertical (y) positions of the manipulandum mapped to the cursor. Reconstruction error of position at a single time bin, t, was also calculated as a function of (1) the total length of time, $T_{pre}$, in which spike trains were observed and (2) the number of neurons included in the analysis. The dependence of the estimation error on $T_{pre}$ was examined by simply recalculating $r^2$ for each value of $T_{pre}$ (See FIG. 18, panel(c)). The analysis of $r^2$ vs. the number of cells is slightly more complicated, as the regression error is not only a function of how many cells one chooses to observe, but also which subset of cells is chosen. Therefore, neurons from a simultaneously recorded data set were randomly selected and the range of $r^2$ obtained for each such randomly selected subset was plotted, using the equation $E(r^2) = \sigma_{ns}{}^t \sigma_{ss}{}^{-1} \sigma_{ns}$. This equation gives the expected $r^2$ given that the covariance matrix of S is $\sigma_{ss}$ and the cross-correlation between N and S is $\sigma_{ns}$. N is a vector-valued signal, with each element corresponding to the firing rate of a single cell, $^t$ denotes transpose, and E(.) denotes expectation not sample mean, as above. Note that $E(r^2)$ depends only on the second-order properties of the probability distribution from which the data were drawn. Data were also examined with a frequency domain regression analysis to compare the information present in hand motion with that available in MI firing. This analysis leads to a measure of signal to noise ratio that can be compared across neurons for different frequencies of hand motion. Neural and position signals were Fourier transformed, and the neural Fourier coefficients at a given frequency $\omega$, $\hat{N}(\omega)$ were regressed onto the coefficients of position, $\hat{S}(\omega)$, to obtain the reconstruction of S at $\omega$, $\hat{R}(\omega)$. Quality of reconstruction was plotted as the signal-to-noise ratios obtained at each frequency:

$$SNR(\omega) = \frac{E(\hat{S}(\omega) * \hat{S}(\omega))}{E((\hat{S}(\omega) - \hat{R}(\omega)) * (\hat{S}(\omega) - \hat{R}(\omega)))}, \quad (5)$$

where E(.) denotes the sample mean (where the number of samples here is equal to the number of trials, typically ~100-200 in these experiments), and complex conjugate.

Results

Eleven data sets from three monkeys were used for analysis, some of the data for which are shown in Table 1. Continuous tracking meeting the conditions of the task was recorded for 6-17 minutes (mean 10.9) for 4-21 neurons (see Table 1). In addition, one monkey performed a standard radial task so that behavior and neural activity could be compared to that in the pursuit tracking task (PTT).

TABLE 1

| Experiment | Time Observed (Minutes) | RMS Velocity (cm/s) | Cells Analyzed | $r^2$(x), $r^2$(y) (full) | $r^2$(x), $r^2$(y) (causal) |
| --- | --- | --- | --- | --- | --- |
| 1 | 8 | 4.6 | 5 | 0.36, 0.16 | 0.16, 0.09 |
| 2 | 8 | 4.7 | 5 | 0.46, 0.16 | 0.26, 0.09 |
| 3 | 12 | 4.6 | 4 | 0.11, 0.04 | 0.03, 0.02 |
| 4 | 11 | 3.4 | 14 | 0.49, 0.19 | 0.27, 0.11 |
| 5 | 11 | 3.2 | 14 | 0.61, 0.40 | 0.46, 0.17 |
| 6 | 13 | 2.5 | 8 | 0.40, 0.15 | 0.28, 0.12 |
| 7 | 17 | 3.0 | 18 | 0.54, 0.48 | 0.44, 0.43 |
| 8 | 7 | 2.6 | 21 | 0.32, 0.46 | 0.30, 0.35 |
| 9 | 6 | 2.5 | 8 | 0.11, 0.21 | 0.10, 0.10 |
| 10 | 13 | 2.5 | 11 | 0.19, 0.24 | 0.13, 0.17 |
| 11 | 14 | 2.9 | 17 | 0.27, 0.37 | 0.19, 0.30 |

Pursuit Tracking Task

The continuous tracking and the direction tasks vary considerably in the extent of parametric space explored, the dependence among variables and stationarity of the kinematic and neural signals. FIGS. 1A-1D illustrate kinematic and neural activity data obtained in a radial task from one monkey to provide comparison with the continuous task shown in FIGS. 2-5.

The "center-out" task. FIG. 1A is a scatter plot of hand positions observed during the movement phase of the experiment, illustrating the uneven sampling of the workspace in this task. Dots are spaced 10 ms apart. FIG. 1B is a scatter plot of horizontal hand position vs. velocity. Note the strong statistical dependence between these two variables. FIG. 1C is a plot of average (SD) tangential hand velocity for all trials in FIGS. 1A-1B, aligned on the "go" cue; note the strong dependence of the average speed on the time t since the beginning of the trial. FIG. 1D shows a typical MI single neuron peri-event time histogram (PETH), showing, as in FIG. 1C, strong nonstationarity with respect to time.

The direction task, by design, results in movements from a constant location to one of a fixed set of 8 discrete locations.

There is no specific trajectory requirement other than the need to end at a specific location within task time constraints. Movements on any given trial are typically reduced to target direction, which is a reasonable approximation because point to point arm movements in primates are nearly straight. However, FIG. 2A shows that truly straight motions rarely occur, and many time varying features of hand motion can be lost when only target location coding is considered. Further, there are strong correlations between position and velocity, (see FIG. 1B) so that these variables can not be considered as independent. Other kinematic features are correlated across the experiment. In particular, hand speed is always highly correlated with movement onset (see FIG. 1C), irrespective of direction. These multiple dependencies make it difficult to associate particular motor variables with the underlying neural activity. Neural activity in such tasks is also non-stationary. Firing across the experiment is systematically higher after the go cue and is correlated with hand speed change.

Figure 2:
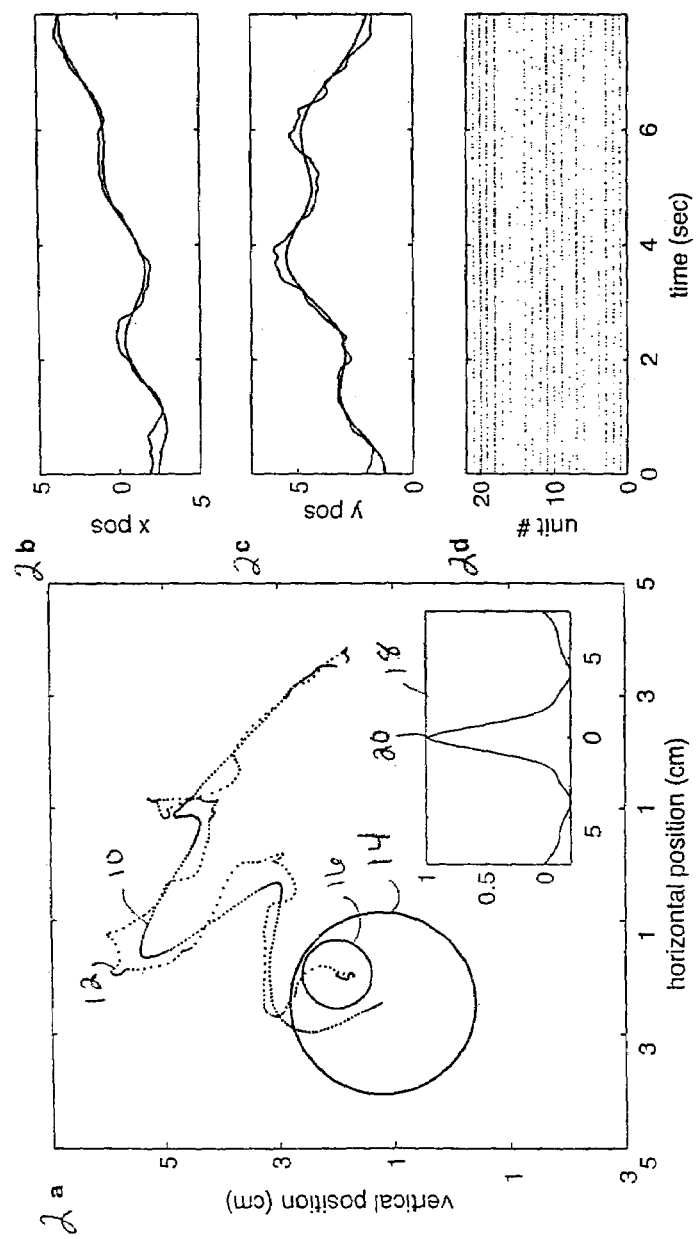
FIGS. 2A-2D show the continuous tracking task.
Figure 3:
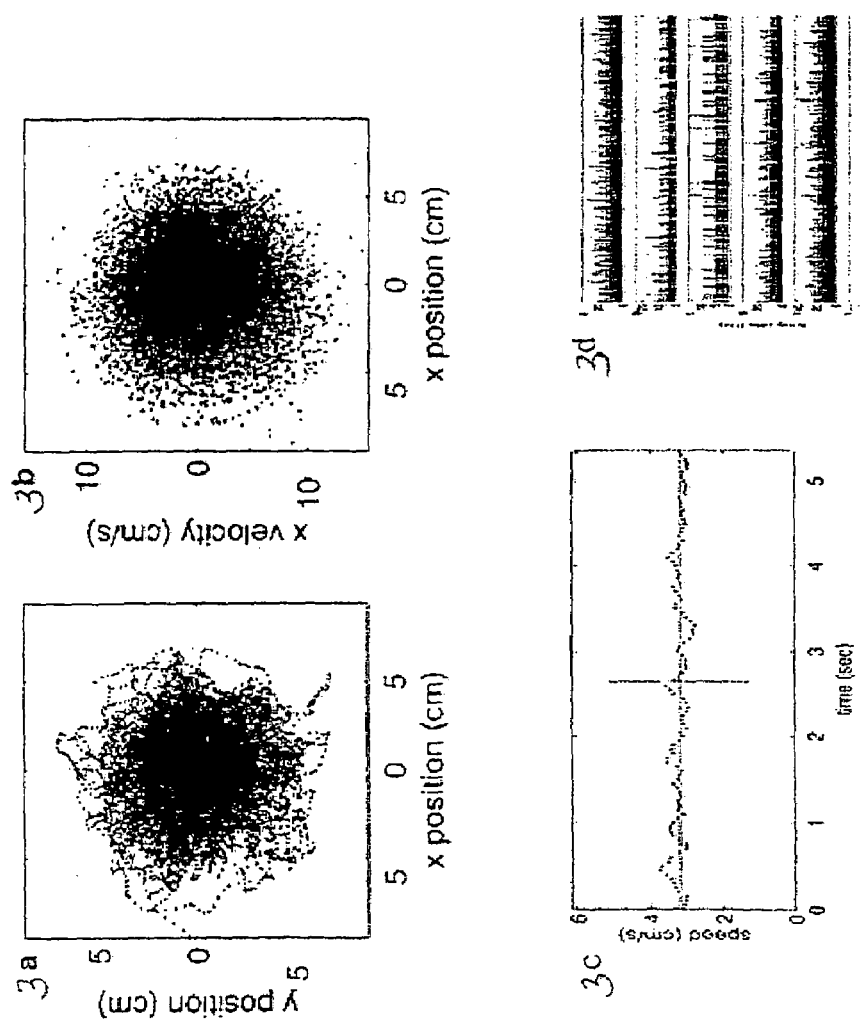
FIGS. 3A-3D are a summary of behavioral data for one experiment.
Figure 4:
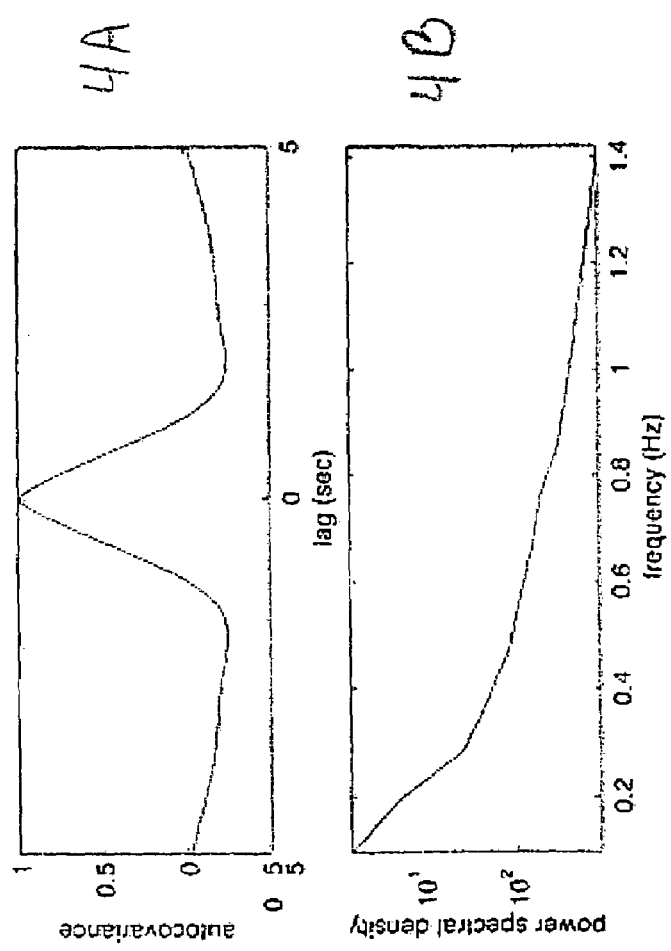
FIGS. 4A-4B show temporal properties of the hand position signal for one experiment.

By contrast, the PTT covers a large kinematic space and it achieves considerably improved independence of kinematic variables and stationarity of kinematic and neural activity (FIGS. 2-4). FIG. 2A provides an example of continuous tracking performance for a single trial. Tracking episodes lasted 4-8 seconds; during this time the hand tracked the visual cue within the limits of the task, except for occasional pauses in tracking (clustered points on and path). Continuous tracking movements were largely determined by the visual stimulus, as demonstrated by the close temporal relationship of the hand and visual cue shown in the FIG. 2A inset. The peak of this cross-covariance was located within 50 ms of zero lag and the peak correlation coefficient across all data sets exceeded 0.97. The relatively high tracking accuracy over time can be appreciated in plots of x and y position/time across a trial (FIG. 2B). Tracking movements were slow, generally smooth, and distributed across velocity and position in a Gaussian manner, as set by the distribution of the stimulus signal. Mean hand RMS speed across all experiments ranged from 2.5 to 4.7 cm/sec across the set of experiments used (Table 1) and nearly all of the power was <1 Hz (FIG. 4A). FIG. 2 shows the continuous tracking task. FIG. 2A shows the path taken by visual stimulus 10 and hand 12, plotted as horizontal vs. vertical position. Dots are spaced 10 ms apart. This trial was taken from an experiment in which the RMS hand velocity was a relatively slow 2.6 cm/s (see Table 1). The large circle 14 indicates the perimeter of the visual target, and the small circle 16 the feedback cursor. Inset 18 is the cross-covariance between the horizontal positions of the visual target and hand; the peak 20 of this curve is located at zero seconds and has a value quite close to unity, indicating that the hand position at any time t is tightly linked with the target position at the same moment. FIG. 2B shows horizontal and FIG. 2C vertical position vs. time. These plots give a better sense of the smoothness of the position signal. FIG. 2D is raster plots of neural activity of 21 neurons recorded during this trial. Each row represents one neuron; each tick mark represents one action potential.

Figure 1:
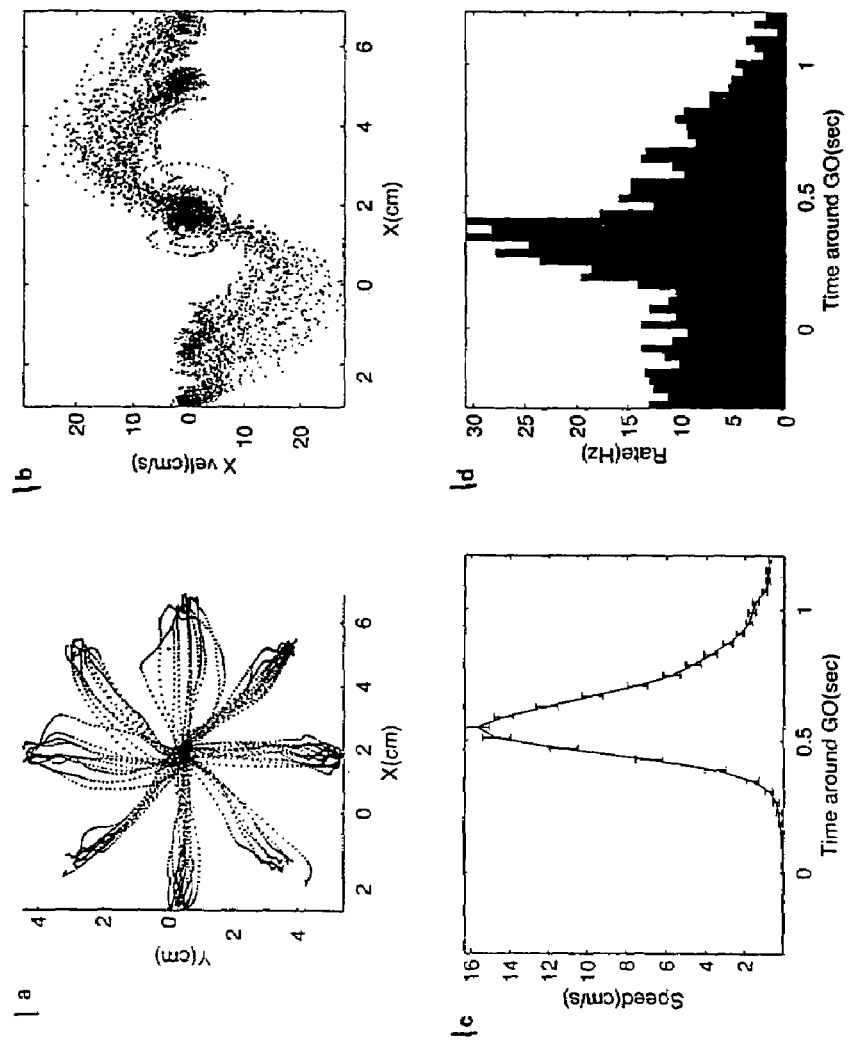
FIGS. 1A-1D illustrate kinematic and neural activity data obtained in a radial direction task from one monkey.

FIG. 2 demonstrates that the continuous task more completely sampled kinematic space (FIG. 2A) and decoupled hand position and velocity across the experiment compared to the radial task (compare with FIG. 1). Further, the observed joint distributions of horizontal vs. vertical hand position, the horizontal and vertical components of hand velocity and the horizontal position vs. the horizontal velocity were not correlated. No significant correlation was observed between any of the pairs of velocity and position variables (Pearson test; p<0.05). Table 2 lists the symbols and their definitions used herein.

TABLE 2

| Symbol | Definition |
| --- | --- |
| MI | primary motor cortex |
| PETH | peri-event (e.g., "go" cue) time histogram |
| $\tau$ | lag (time elapsed since a given action potential) |
| t | time relative to the start of the behavioral trial (to be distinguished from $\tau$) |
| $T_{pre}$ ($T_{post}$) | time before (resp. after) the current time t used to estimate the current position |
| N(.) | neural firing rate, as a function of, e.g., time t, or hand position ($\rho$, $\theta$) |
| S(.) | behavioral signal (e.g., hand position or tangential velocity) |
| ($\rho$, $\theta$) | polar coordinates: radius and direction |
| TL | target location in the "center-out" task |
| C | number of cells observed |
| $\hat{}$ | Fourier transform |
| r, $r^2$ | standard measures of regression error (normalized mean-square error) |
| $\varrho$ | Pearson correlation coefficient |
| I(x; y) | mutual information between the random variables x and y |

Hand speed and neural activity are effectively stationary across the task. Mean hand speed does not vary as a function of time (compare FIG. 3C and FIG. 1C) and average firing rate does not depend on the time relative to the start of tracking (compare FIG. 1D and FIG. 3C). When neural activity is averaged over all trials to construct a peri-event time histogram (PETH) for a given cell (aligned on the start of tracking, i.e. t=0 in FIG. 2), the average firing rate at time i is the same as at time j, for all times 0<i, j <T (FIG. 3D where T is the length of the trial (test on correlation with linear trend over the first or last 2.5 seconds of the trial; p <.05). Thus, the stationarity makes it possible to treat each spike throughout a trial in a uniform manner as an independent sample. In step tracking tasks, data must be divided with some level of uncertainty into behaviorally defined epochs in an attempt to capture stationary periods of neural activity. This makes it difficult to compare data across epochs and many statistical methods are not valid if applied across non-stationarities.

FIGS. 3A-3D are a summary of behavioral and neural data for one experiment, including variable distribution for kinematics, speed and firing. FIG. 3A are scatter plots of horizontal and vertical hand position and FIG. 3B are plots of horizontal hand position and horizontal velocity. Note the evenness of sampling and the lack of correlations between any of these pairs of variables (c.f. FIGS. 3A-3B). FIG. 3C is stationarity of tangential hand speed during tracking. The trial-averaged speed as a function of time, t, since the start of the tracking period shows only small fluctuations around the mean speed across the entire experiment (FIG. 3C Horizontal line indicates mean speed; vertical line indicates SD). Compare with the large modulations seen in the radial task, FIG. 1D. Black lines indicate the mean (SD).

The joint distributions of hand position and velocity generally approximated a Gaussian distributions with zero covariance (modified Kolmogorov-Smirnov test; p<0.05). The overall smoothness of hand movement during tracking is evident in the autocovariogram of FIG. 3A, and the power spectrum of horizontal hand position in FIG. 4B. However, zero velocities were observed slightly more frequently for the slowest RMS velocity (2.5 cm/s), than predicted by the Gaussian model, suggestive of some intermittency in tracking at slow speeds. FIGS. 4A-4B show temporal properties of the hand position signal. FIG. 4A is the auto-covariance and FIG. 4B the power spectrum of the horizontal hand position, emphasizing the slow time scale of this signal.

Neural Activity During Tracking

Figure 5:
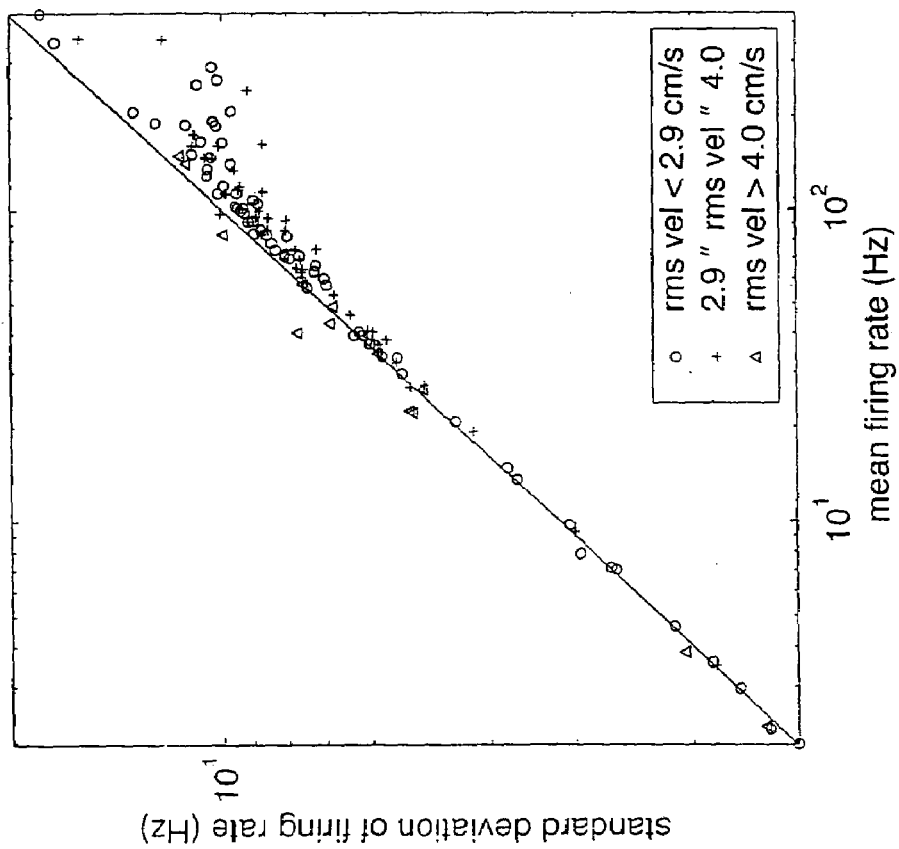
FIG. 5 shows a Poisson fit for firing.

Across the 11, experiments between 4 and 21 (mean 32 11) well-isolated single units were simultaneously recorded (see Table 1). In all, 125 cells were analyzed. FIG. 2D shows a representative example of the spike-trains of 21 cells, recorded simultaneously during a single tracking trial. Qualitatively speaking, these randomly selected MI neurons showed low overall mean firing rates and less pronounced modulation illustrated by others in step tracking tasks. The low firing rate regime of these cells was not intrinsic to these neurons; when the same neurons were recorded in the center out task they showed marked rate modulations as typically found in MI (see FIG. 1D). Neural activity during continuous tracking approximated a Poisson process (see FIG. 5). The mean and variance of the firing rate (spike counts per 50 ms bin) are highly correlated over this range for rates <10 Hz, the relationship between the spike count mean and variance is largely linear with unity slope. For higher firing rates, the Fano factor (the ratio of the variance to the mean) falls slightly below the unity level, on average. The spiking process was therefore considered as Poisson random variable because it fit this process. FIG. 5 also shows that there is no overall correlations RMS hand speed and average firing rate (or the variance of the firing rate) and the (Spearman rank-order correlation coefficient; p<:05), which further demonstrates the validity of the assumption that firing rate can be considered as independent samples of a stationary process. FIG. 5 shows a Poisson fit for firing. Each point corresponds to the mean and standard deviation of the firing rate of a single neuron; note the large range of firing rates. The line shows the expected relationship between the mean and standard deviation for a Poisson random variable (recall that a square root function appears as line of slope one-half on a log-log scale). The Poisson line gives a good fit to the data at lower firing rates, but is not quite sufficient at higher rates, where the Fano factor falls well below the unity level, on average. No clustering of firing rate (or variance) with RMS tangential hand velocity is apparent.

Spatio-Temporal Tuning

Given these properties of the data it is possible to define MI spatiotemporal tuning functions—that is, the time varying tuning of the cell with respect to a particular kinematic variable as described in the methods section above. Spatial and temporal features of tuning for single MI neurons were examined for velocity and position (denoted $N(\vec{v},\tau)$ and $N(\vec{p},\tau)$, respectively). These functions summarize a neuron's instantaneous firing rate-dependence on hand velocity $\vec{v}$ or position $\vec{p}$, as well as the time varying features of tuning ($\tau$), the time difference between hand motion and the observed firing rate sample. A lag (+$\tau$) is the amount of time the neuron was firing in advance of that kinematic measure; a (−$\tau$)represents a lead. Thus, these functions summarize a neuron's firing rate dependence on hand velocity v or position p at times before the hand moved at a given velocity or was located at the given position.

Figure 6:
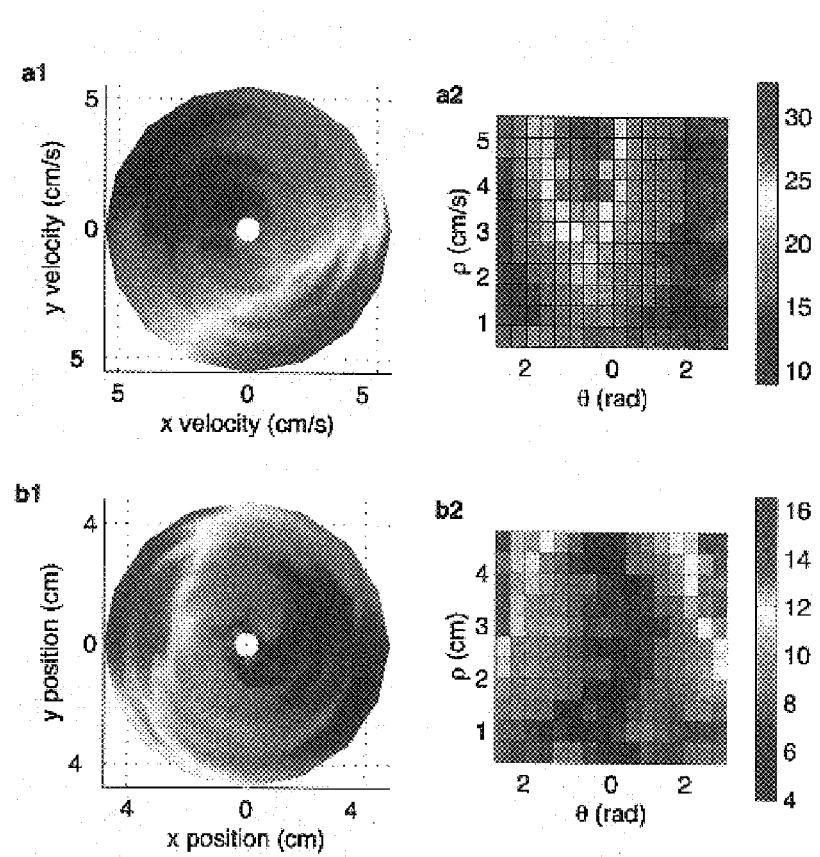
FIGS. 6A-6B illustrate velocity and position spatial tuning plotted first in rectangular coordinates and then transformed into polar coordinates

FIGS. 6A-6B illustrate velocity and position spatial tuning at a single value of $\tau$ plotted first in rectangular coordinates and then transformed into polar coordinates, which is used in the remaining representations of tuning functions. FIGS. 6A-6B depict direction tuning which fits a commonly observed tuning.

In FIG. 6A, the tuning surface in rectangular coordinates is shown, and in FIG. 6B the same object is presented in polar coordinates. Firing rates are measured in Hz. This neuron is strongly tuned for hand velocities to the right. Note that the tuning visibly improves with increasing speed. The origin for these N(v) surfaces is taken as (0,0) (see Methods section above). This cell is approximately cosine-tuned for direction, i.e., the function is well-approximated by a sinusoid for any fixed speed. In fact, the phase of this sinusoid is constant as a function of θ, so that the direction tuning curve N_v(a, v {1}{R} 0^R N_v(a, d for R sufficiently large) is also sinusoidal. Finally, the amplitude of the tuning curve scales with speed, so that the cell is, in a sense, more strongly tuned for direction at higher tangential velocities. Panel (c) shows this cell's tuning for target location (TL) in the center-out task (recorded on randomly interleaved trials); for this cell, the TL-tuning curve and velocity tuning function N(v) match well.

Analogous tuning functions for hand position can also be derived, as shown for a different neuron in FIG. 6B. In Cartesian coordinates, this neuron has a restricted region of firing in position space. When transformed to polar coordinates, sinusoidal tuning of θ (angle) similar to velocity tuning is evident. Amplitude increases with ρ (distance from center) but maintains constant phase.

If ρ scales linearly, this putative coding dimension could be interpreted as a gain function of θ which would best fit a planar model. A better fit to a Gaussian model would reject planar tuning structure. A planar model significantly fits MI tuning functions for both velocity and position for 65 neurons. The more general mutual information test (discussed below) identified the same proportion of cells, indicating that all cells with significant position and velocity tuning have planar tuning functions. Two-dimensional Gaussian functions never provided a better fit (despite the fact that the Gaussian function had three extra free parameters). In all cases the Gaussian was near-planar (i.e. flat) and peaked outside the observed workspace edge. Thus, the simple model in equation (6), above, captures the two-dimensional tuning for both position and velocity.

Figure 7:
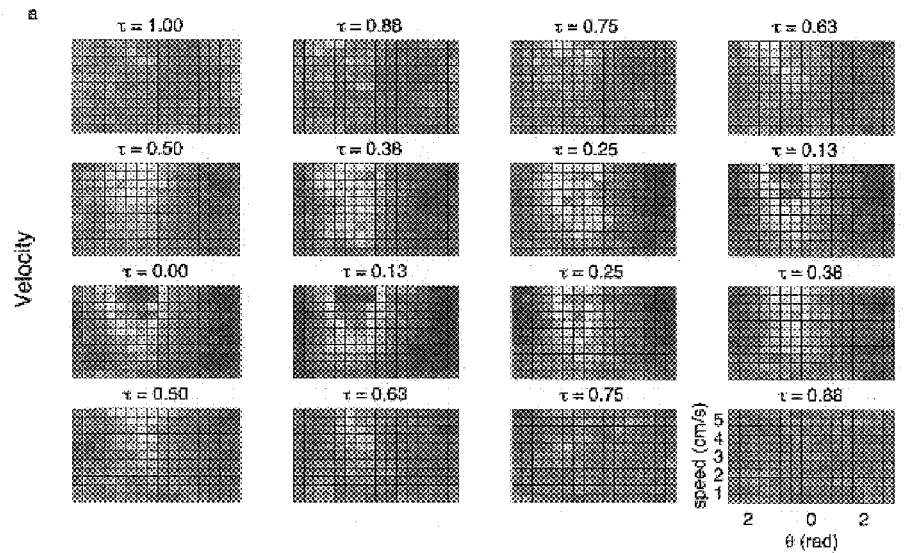
FIGS. 7A-7B depict the most common MI tuning characteristics.
Figure 7:
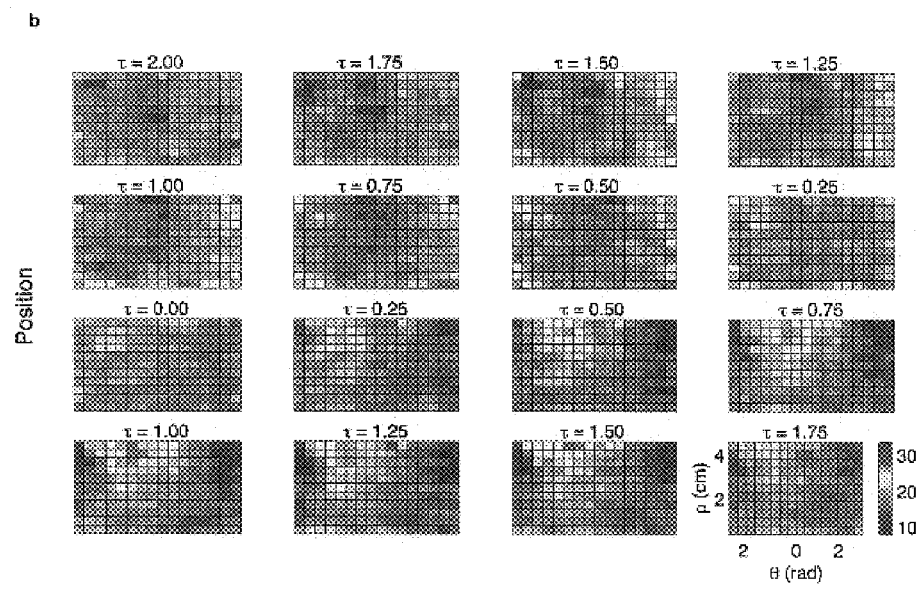
Figure 8:
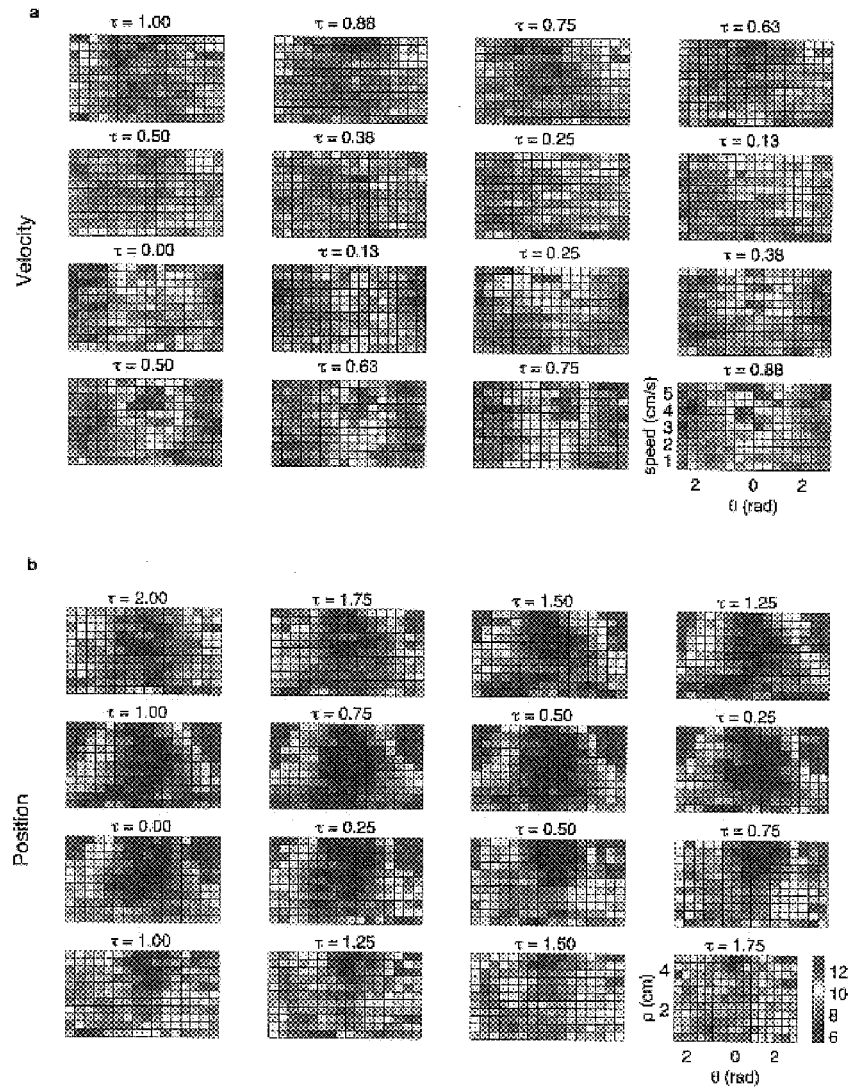
FIGS. 8A-8B show spatiotemporal tuning curves in a position-tuned cell.
Figure 9:
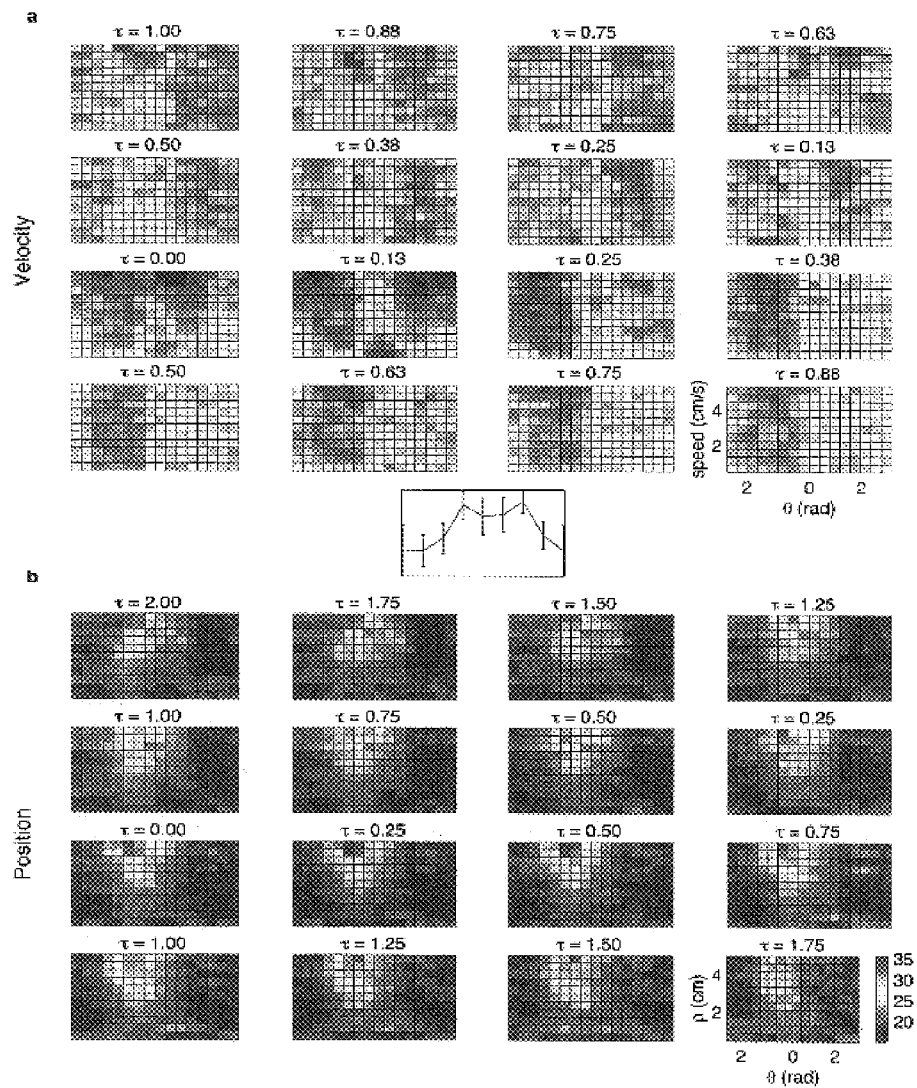
FIGS. 9A-9B show another example of a position-tuned cell.

The data in FIGS. 6A-6B only reveal the tuning function for a single time point. FIGS. 7-9 show examples of how spatial tuning functions for velocity, $N(\vec{v},\tau)$, and position, $N(\vec{p},\tau)$, evolve over time and illustrate tuning function heterogeneity. FIGS. 7A-7B depict the most common MI tuning characteristics. First, the cell is strongly velocity-tuned, especially at positive lags $\tau$>0. Second, the firing rate peaks (red) approximately 100 ms prior to the time at which the velocity was measured. Tuning begins to emerge several hundred milliseconds prior to this time and fades several hundred milliseconds afterwards. Throughout this time the overall structures remains similar in phase. The temporal structure of this velocity tuning function $N(\vec{v},\tau)$ is largely explained by a modification of (6):

$$N_v(\rho,\theta) \approx a_0 + a_1(\tau)\rho\cos(\theta - \theta_{PD}) \quad (7)$$

where $a_1(\tau)$ is a smooth, nonnegative function of $\tau$, with a maximum at 100 ms, such that $a_1(\tau) \approx 0$ for $|\tau|>1$ second. The cell shown in FIGS. 7A-7B shows strong velocity tuning, peaking near 100 ms, with "echoes" seen in the position domain. The color scale is the same for all subpanels; firing rates are measured in Hz.

Position tuning also showed a spatiotemporal structure that appeared to be directly related to velocity tuning for some neurons, but independent for others. The position tuning $N(\vec{p},\tau)$ of the neuron in FIG. 7 follows directly from its velocity tuning. The neuron shows firing restricted to some positions that varies across time. This form of position tuning can be explained from inherent dependencies of hand velocity and position when considered as time-varying signals (although not, as static variables, see FIG. 3). Given rightward hand movement at time t=0 and that the range of hand positions is bounded by the size of the tablet, the mean position at time t=−ϵ will be to the left of the mean position at time t=+ϵ, for all sufficiently small positive times ϵ. Different time scales for position and velocity curves can be attributed to the longer position autocorrelation compared to velocity. Thus, if we have a neuron signaling rightward motion of the hand at τ=100 ms, we should expect this neuron, by extension, to signal the leftward position of the hand at negative time lags (τ<0 ms, i.e. in the future), and the rightward position at more positive lags (τ>200 ms, i.e. in the past), as observed here. Therefore, for neurons with these types of spatiotemporal tuning functions, position tuning is parsimoniously explained in terms of velocity tuning.

FIGS. 8A-8B show spatiotemporal tuning curves in a position-tuned cell. The velocity tuning of this cell is visibly weaker than that of the cells shown in the previous figure, while the position tuning is quite strong. Note how the preferred, direction in velocity space flips completely from lead to lagged times, while the position PD remains nearly constant over the four seconds observed here. Conventions are as in FIG. 7.

FIGS. 9A-9B show another example of a position-tuned cell. Note the late occurrence of the peak in velocity tuning, at 500 ms. Velocity tuning reverses without correlated shift in position tuning. Inset shows the directional tuning of this cell obtained in the radial task (SD). The radial tuning of this cell agrees well with the position tuning obtained during tracking; conventions are as in FIG. 7.

Figure 10:
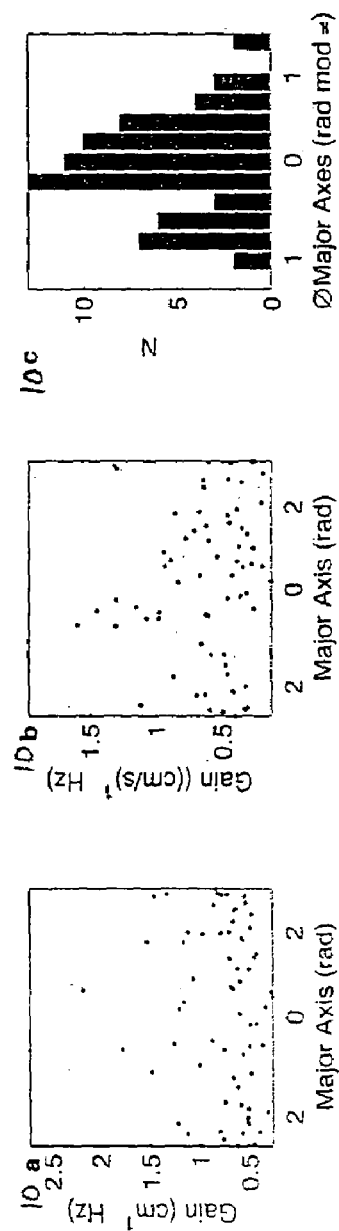
FIGS. 10A-10C summarize the spatial aspects of the velocity and position tuning curves over all neurons recorded.

In contrast to FIG. 7, FIGS. 8 and 9 show neurons whose position tuning cannot be readily explained from the cell's velocity tuning, suggesting that they specifically encode position separately from velocity. In these examples, position tuning is pronounced and more temporally invariant than velocity. In FIG. 8, the position tuning curve nearly peaks at large ρ and θ=±2π, but the velocity tuning curve flips by 180 degrees between τ=−1 and τ=0.88 seconds, completely opposite to the effect shown in FIG. 7. For the neuron in FIG. 9, the peak in position tuning occurs at large ρ and θ=−π/4, while the velocity tuning peak shifts from θ=−π/4 to θ=π/2 from τ=−1 to τ=0.88 seconds. Having recorded this cell during an experiment in which continuous tracking and center out trials were intermingled, we can observe that the latter direction tuning (inset, FIG. 9A) matches closely that predicted by integrating the spatiotemporal tuning function over τ. FIGS. 10A-10C summarize the spatial aspects of the velocity and position tuning curves over all neurons recorded. The peak velocity (FIG. 10A) and position tuning (FIG. 10B) in the (ρ,θ) space scatter plots demonstrate a rather uniform distribution across the kinematic space. This distribution indicates that neurons dominated by strong position and velocity tuning are not distinct classes, but appear to be distributed continuously. FIGS. 10A-10B are scatter plots of the major axis and planar angle of single cells, represented radially, in position (FIG. 10A) and velocity (FIG. 10B) space. As an example, if a neuron had a major position axis of 0 degrees (i.e., the neuron fired at a higher rate when the hand was on the right than when on the left) and a planar angle of one, the corresponding point would appear in FIG. 10A at (1,0) in Cartesian coordinates. Only neurons with significant planar fits for both position and velocity are analyzed here (N=81).

FIG. 10C shows the observed distribution of the differences between the velocity and position major axes; note the peak at zero.

Information-Theoretic Analysis

Figure 11:
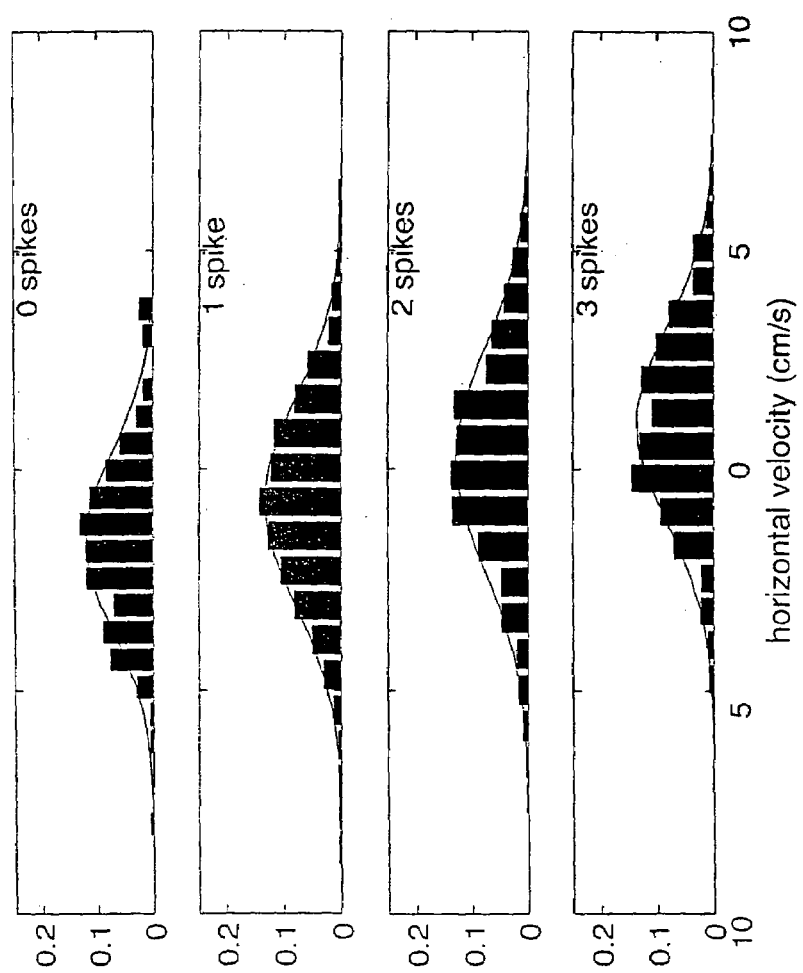
FIGS. 11A-11D show the conditional probability distributions with corresponding Gaussian fits of the horizontal hand velocity.

Information theoretic analysis can be used to provide a direct measure of the amount of position and velocity information in these neurons; further, the tracking task provides a format to describe the temporal evolution of this information in MI neurons. The results of FIGS. 6-9 demonstrate that, by observing the position or velocity of the hand, it is possible to derive information about the activity of a given MI neuron. The converse, by Bayes' law, is also true, information about position or velocity can be derived from the MI firing rate. FIG. 11 provides one example of how well observations of a cell's firing rate can be used to predict the hand velocity. FIGS. 11A-11D show the conditional probability distributions with corresponding Gaussian fits of the horizontal hand velocity at t+τ, τ=100 ms given that this cell fired zero, one, two, or three spikes within a 50 ms window around time t. This demonstrates that, for MI neurons, firing rate typically conveys highly ambiguous information with small firing rates. The firing rate of this neuron clearly bears information about the horizontal hand velocity: if the neuron fires at a high rate, it is more probable that the hand is moving to the right, and vice versa.

Figure 12:
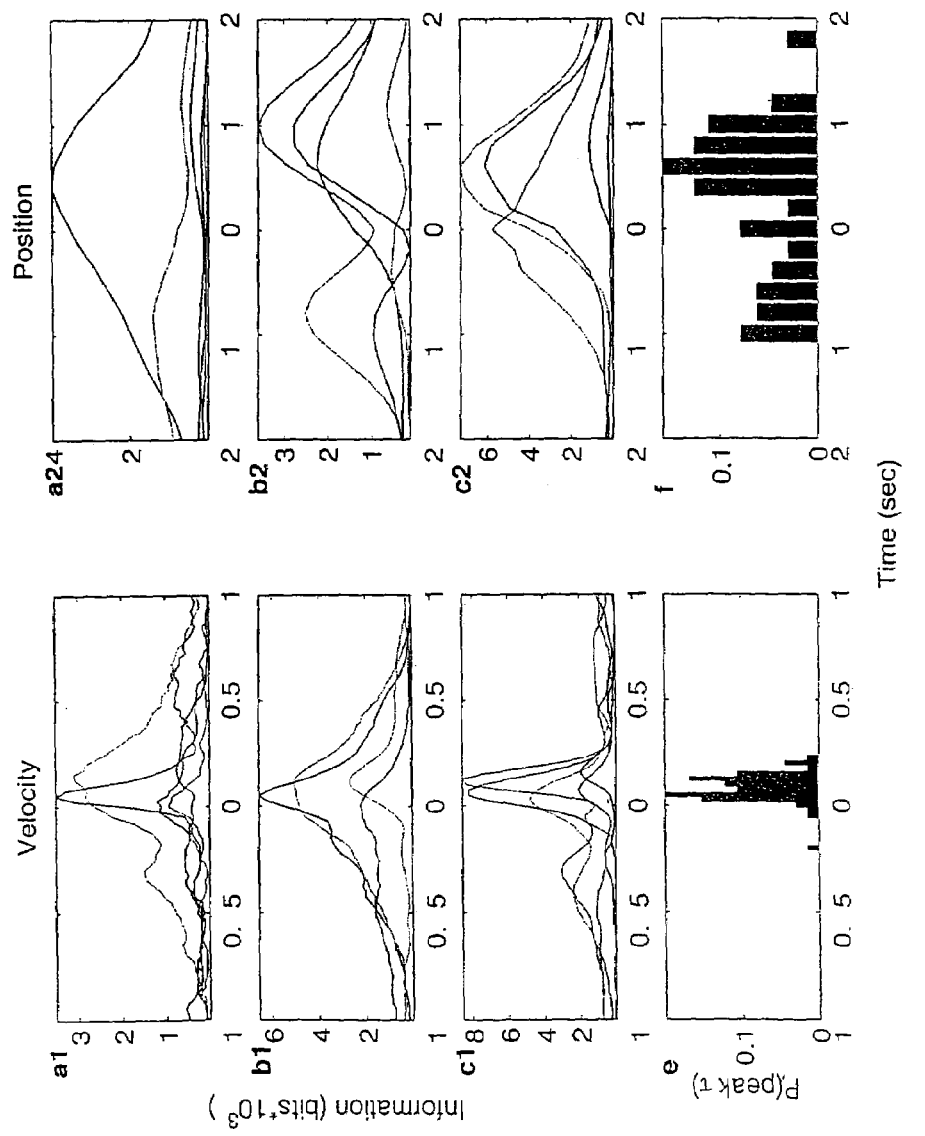
FIG. 12 shows examples of information curves for hand velocity and position.

These probability distributions can be used to derive quantitatively and objectively temporal tuning properties of individual neurons. For this analysis the mutual information between the cell's firing rate and the kinematics of the hand is computed as a function of τ, I(N(0); S(τ)) (see the Methods section above). Here N(0) represents the cell's activity in a given short time interval (here, 5 ms) and S(τ) denotes the value of position or velocity some time τ before or after the current time, t=0. This information statistic is an objective measure of how well these neurons are tuned for these behavioral variables; the more tuned a given cell is at a given value of τ, the more highly separated are the probability distributions corresponding to those shown in FIG. 11, and the higher the value of I(N(0); S(τ)). This quantity does not depend upon any underlying assumptions about the linearity of the relationship between the neural firing rate and the behavioral variable, as do standard correlational statistics. The resulting curves, as functions of τ, discard all spatial tuning properties (e.g., preferred direction) and therefore show only temporal (τ-dependent) tuning features. FIG. 12 shows examples of these information curves for hand velocity (panels (a1), (b1), and (c1)) and position ((a2), (b2), and (c2)). Information was calculated in 5 ms bins. Panels (a1-2) are taken from an experiment with a RMS tangential velocity of 2.5 cm/s, (b1-2) from an experiment with RMS velocity 2.9 cm/s, and (c1-2) 4.7 cm/s. Note the differences in time scale. Panels (d-e) are histograms of the peak for these information curves, taken over all cells whose tuning was strong enough that a well-defined peak existed. The peaks of the velocity curves consistently occur near 100 ms, while the position peak locations are more variable.

Temporal tuning curves are heterogeneous, especially in the position domain; examples of simultaneously recorded neurons in three experiments are shown in FIG. 12, panels (a)-(c). The curves can be umnimodal or multimodal with peaks at τ>0 or τ<0 within the same set of simultaneously recorded data. The widths and shapes of the curves vary widely and there does not appear to be any simple relationship between the curves for velocity and position. Position curves change more slowly than velocity, but this feature obtains from each signal's autocovariance structure, as described above. The width of the velocity information curves is uncorrelated with those of the corresponding position curve (Spearman's rank order correlation coefficient, p<0.05 performed only on the 77 best tuned cells having peak velocity and position information content>0.0005 bits), indicating that they are not directly related to each other The heterogeneity of temporal tuning depicted in each pair of panels (a1,2, etc.) can be directly compared because they were formed from data obtained in the same experiment. This analysis also showed differences in the time at which peak information was available about different hand kinematics. Velocity curves consistently peak near τ=100 ms, while position peaks are more temporally dispersed before and τ=100 ms (panels d and f).

FIGS. 13A-13B summarize the distribution of information values for velocity and position of MI cells and confirms the considerable position and velocity heterogeneity suggested by FIGS. 7-9. Information content ranges over two orders of magnitude. A weak but statistically significant correlation was present between velocity and position information content (Spearman's rank order correlation coefficient=0.17; p<0.05). Moreover, information values by RMS hand speed during the experiment did not cluster (Spearman's rank order correlation coefficient; p<0.05), indicating that speed tuning is an intrinsic property of these cells, independent of the details of the stimulus ensemble used. On average, cells carry only 10% more information for velocity than for position. Neurons with low average activity could convey as much information as those with high average firing rates, indicating that there is no dependence of information content on mean firing rate (FIG. 13b; Spearman's rank order correlation coefficient=–0.06 n.s.). By extension, the information content of a given cell did not depend on firing rate variance (see FIG. 5). FIG. 13A shows a position vs. velocity information plot for all recorded neurons. Information was calculated in 5 ms bins (see Methods section above). Each point corresponds to a single neuron. Significance level for information values=1*10^-4 bits (dashed line). FIG. 13B shows velocity information vs. mean firing rate plot; no significant correlation is observed.

Signal Reconstruction

Figure 14:
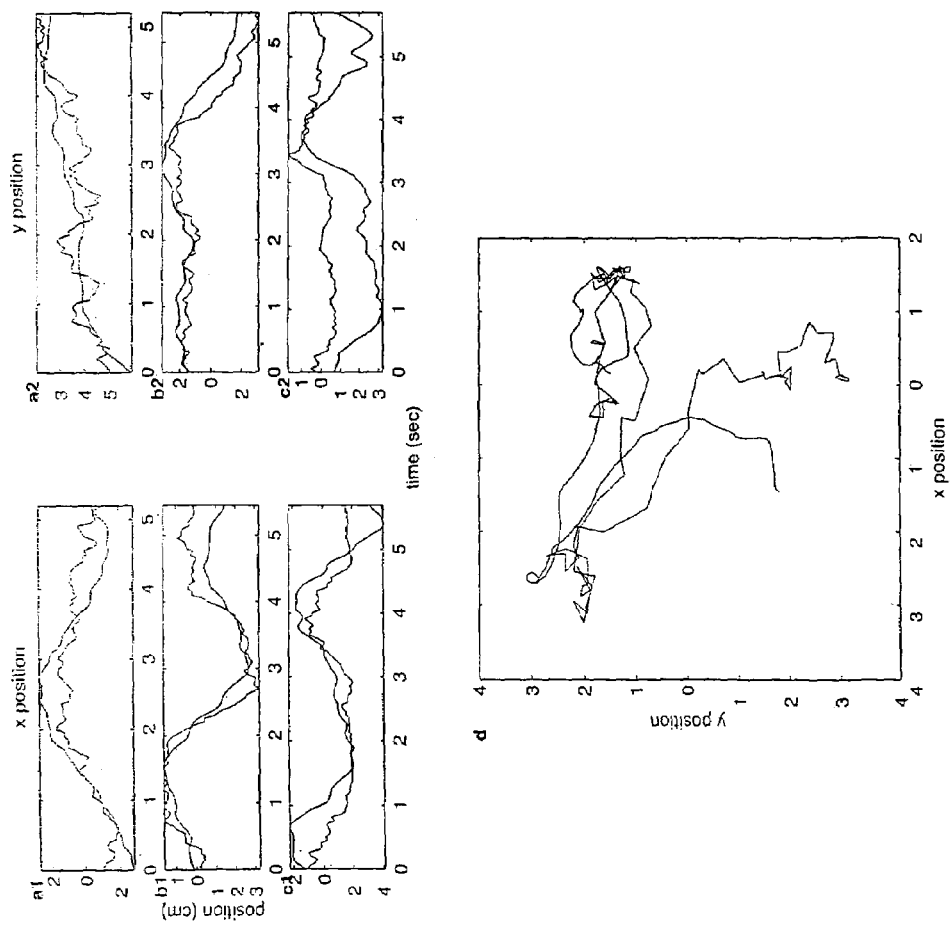
FIG. 14 shows three reconstructed hand paths, with the corresponding true hand paths for comparison.

The analyses above suggest that populations of MI neurons carry information about hand position and velocity. A test of the presence of this information is to attempt to reconstruct hand position using populations of neurons; this is made possible by simultaneous recording of MI neurons and a reconstruction method introduced here. Hand position reconstruction at any given time t was estimated using a weighted linear-combination of the neural activity from all observed cells, some time $T_{pre}$ before and $T_{pos}$ after time t (Paninski, L., Fellows, M., Hatsopoulos, N. & Donoghue, J. Coding dynamic variables in populations of motor cortex. Society for Neuroscience Abstracts 6. 1999, Neter, J., Wasserman, W. & Kutner, M. H. Applied linear statistical models. Irwin, Homewood, Ill. 1985). This linear correlation approach returned a moderately good reconstruction of the hand trajectory with no a priori assumptions (i.e, model) of the tuning process other than what was obtained from the data. FIG. 14 shows three reconstructed hand paths, with the corresponding true hand paths for comparison. The hand paths were reconstructed via the linear regression technique described in the methods section. Reconstructed hand trajectories are plotted in dotted lines, with the true paths in solid lines; horizontal position is depicted on the left, with vertical on the right. Data from three different animals, tracking at different average speeds ((a) RMS velocity=2.5 cm/s, (b) 3.0 cm/s, and (c) 4.7 cm/s). Differences in time scale, compared to velocity are due to the length of reconstruction filters, T_pre+T_post; the beginning and end of the trial was excluded to remove influence by neural data outside of the trial. Panel (d) shows the data from (b) plotted with horizontal vs. vertical position, instead of vs. time. The quality of reconstruction is summarized as a correlation statistic ($r^2$, see Table 1), which provides a reasonable estimate of the fit. The performance of the linear estimator ranged from marginal up to about 60% of variance captured. The data in Table 1 also shows that the observations of neural data after kinematic event occurred (i.e., setting $T_{post}$>0) robustly improves the reconstructions, as expected given the results in FIG. 12 and suggesting feedback of some type onto MI neurons.

Figure 16:
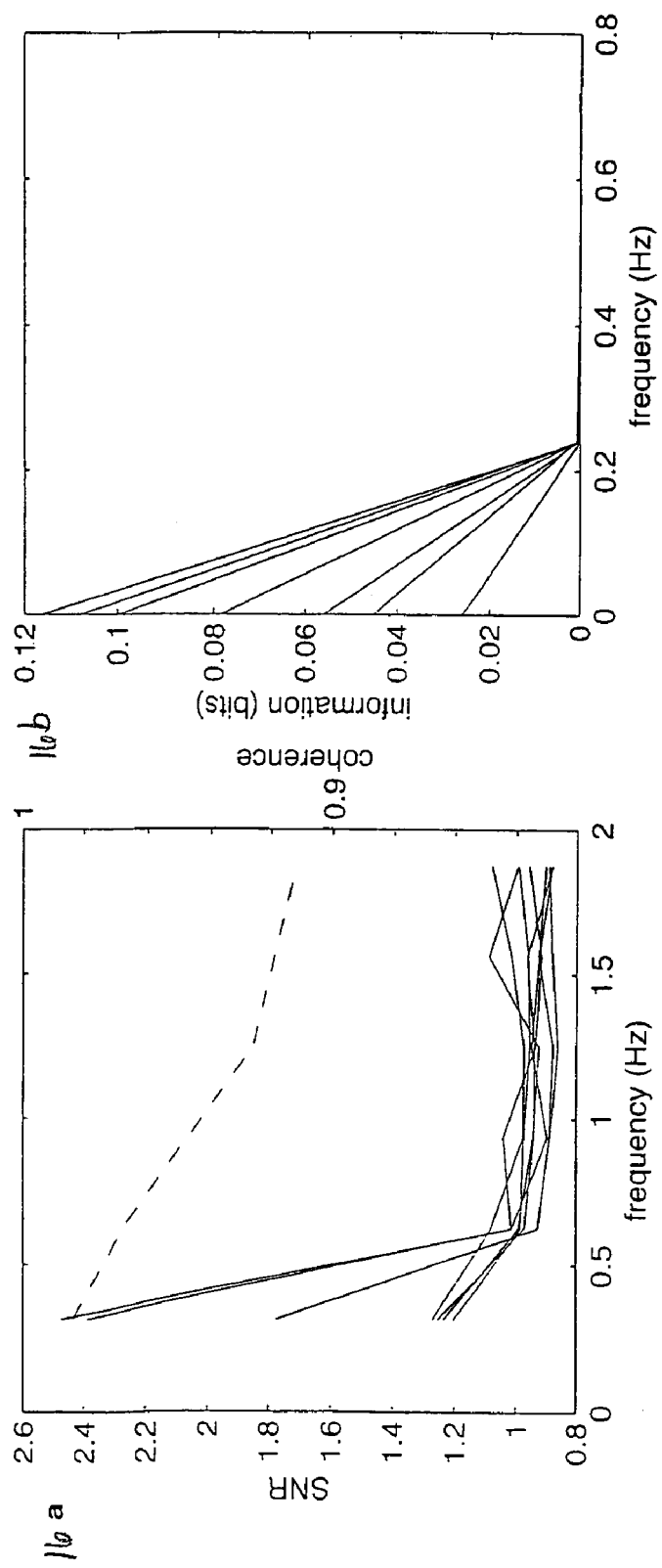
FIGS. 16A-16B are the results of linear regression analysis.

The linear reconstruction technique can be used to quantitatively evaluate which aspects of the tracking are contained in MI activity. The analysis, shown in FIG. 16 demonstrates that MI activity can provide information only about the slower hand trajectory, component, as suggested in FIG. 14. This observation was quantified by reconstructing the position signal directly in the frequency domain. Across the 11 experiments, the signal-to-noise ratio (SNR) of the reconstruction consistently dropped to the unity level by approximately 0.5 Hz, indicating that the linear technique can not extract information about hand position above this frequency (FIG. 16A). By contrast, stimulus tracking includes higher frequencies, as shown in the average coherence plot between the hand and visual target position (dashed line, FIG. 16A). This result was confirmed with nonlinear local frequency information-theoretic approach (see Methods; FIG. 16B), confirming that the lack of any higher-frequency information was not an artifact of the linear analysis.

FIGS. 15A-15B are a signal reconstruction via linear regression. FIG. 15A is a plot of normalized $r^2$ vs. length of filter, T_pre (calculated with strictly causal filters, i.e., T_post=0). This plot illustrates the rise in reconstruction accuracy as neural activity is observed over longer time windows. FIG. 15B is a plot of normalized $r^2$ vs. number of cells, C, included in regression: for any fixed C, $r^2$ values for many randomly chosen subsets of C cells were calculated according to the method described above. The shaded area represents the range of $r^2$ values at each value of C, and emphasizes the dependence of the rate of reconstruction accuracy gain with increasing C on the neurons used for the reconstruction.

Figure 15:
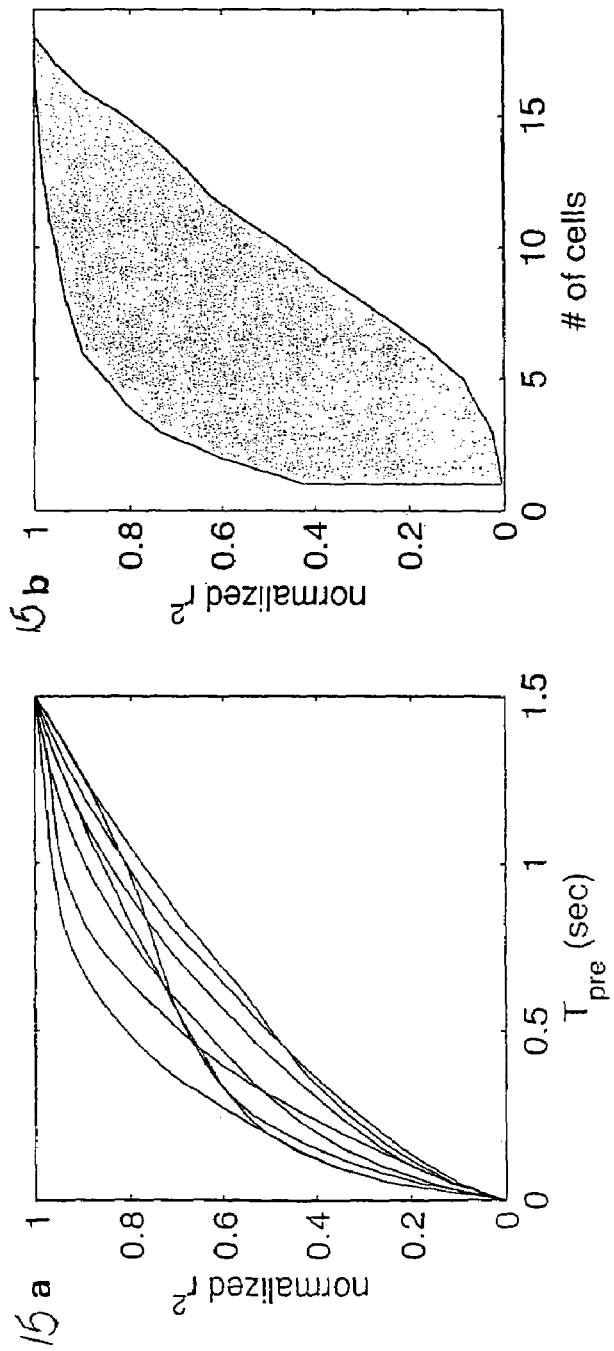
FIGS. 15A-15B are a signal reconstruction via linear regression.

FIGS. 16A-16B are the results of linear regression analysis. FIG. 16A is a plot of signal-to-noise ratio (SNR) attained via linear regression in the frequency domain (solid line), for all experiments with SNR(a=0.2 Hz)>1.2. Note the sharply low-pass nature of these curves. The dashed line shows the coherence between the hand and visual target position signals as a function of frequency; the coherence declines much more slowly than do the SNR curves, indicating that the monkey's hand can track the visual stimulus at higher frequencies than we can track the monkey's hand, given the activity of MI neurons. FIG. 16B shows information content in the frequency domain. This panel confirms the drastically low-pass nature of the information about hand position available in these cells, without the linearity assumptions required for the analysis in FIG. 16A. Also evaluated was the effect of the duration of filters (period of spike observation) and the number of neurons on the quality of reconstruction. As long times were considered, reconstructions improved (see FIG. 15). In order to compare between experiments, the raw $r^2$ values were normalized by the peak $r^2$ observed during the given experiment, so that these curves range from 0 to 1. FIG. 15A gives a sense of the typical trade-off between speed and accuracy in the reconstructions: the more time bins we examine, the better the reconstructions, but at the cost of a greater delay in the reconstruction output. The slope of the graph is quite sharply peaked near zero, indicating a kind of diminishing returns in $T_{pre}$; when $T_{pre}$ is small. Thus a smaller time sample of rate achieves a given increase in $r^2$ when $T_{pre}$ is small. Increasing the number of neurons considered also improves reconstruction. The number of cells observed has a significant positive correlation with reconstruction (Spearman rank-order correlation coefficient; $p<0.05$). However, how this improvement grows depends on which population of cells is observed. The graph in FIG. 15B shows the change in the function as different random samples of the neurons are considered. At their extremes these curves could either be linear or exponential, making it difficult to make any quantitative statements about the asymptotic behavior of the estimator as the number of cells observed becomes larger than those directly measured here (cf. Wessberg, J., et al. Real-time prediction of hand trajectory by ensembles of cortical neurons in primates. Nature 408, 361-365 20).

Discussion

A novel, visually-guided, continuous tracking task was devised and used to describe the spatiotemporal tuning of MI neurons for hand position and velocity and to show that hand motion can be reconstructed from MI activity. This task enabled the identification of three novel features of the relationship between motor cortical activity and hand movement during visually guided tracking. First, the spatial features of MI tuning were described in the context of its temporal evolution. Second, the statistical features of the task permitted quantification of the amount of position and velocity information and identification of their lead-lag relationships. Coupled with multielectrode recording, spatiotemporal tuning functions could be compared for sets of cells recorded under identical behavioral conditions. Finally, the ability to decode hand trajectory using simultaneous, single trial firing rates could be tested with a method derived from linear regression. The results demonstrate that MI has a continuous contribution to visually guided tracking hand motion. This information is provided by a heterogeneous population of neurons that carry position and velocity information. Velocity typically peaks within a narrow temporal window. In contrast, peak position specification is more broadly distributed in time, consistent with feedforward and feedback encoding. In addition they show that MI specifically contains information about low-frequency components of the hand motion during continuous hand motions that are guided by vision. Trajectory information is broadly distributed and small for single cells. However, the information from the firing patterns of small numbers of regionally associated MI neuron populations is sufficient to predict any future hand trajectory.

Continuous Tracking Task

The continuous tracking task (CTT) devised here advances the ability to measure the spatiotemporal tuning of MI neurons and the information they carry about hand motion. It extends knowledge of MI activity to include hand motions that are continuously guided by a visual stimulus with uncertain motion, as might occur in many natural behaviors. The task is novel in that behavior is not drawn from a broad sample of motions rather than a limited, overtrained set. Statistically speaking, the standard center out direction task, has high certainty and considerable planning is possible. Movements are drawn from one of 8 possibilities, always with the same origin and a familiar target. In the CTT only the movement boundaries are constrained; within that world, the upcoming actions are close to random. The fact that directional tuning emerged from the results demonstrates that this feature is not a feature of training, but is generally present in the tuning of MI neurons in a wide range of tasks under a variety of conditions.

The task design permitted the use of a systems analysis approach to define the relationship between movement and neural activity, much as it has been applied to sensory systems. However, generating a broad, unstructured stimulus set (in this case, movements) in the ideal application of this method is a particular challenge for motor systems. The stimuli were largely unpredictable within the constraints of task but were limited by plausible hand motions. Monkeys were able to track the visual stimulus in a generally smooth and continuous manner with minimal lag, consistent with attentive, continuous tracking. This movement is viewed as a collection of time-varying signals where each trajectory forms a novel, time-varying "stimulus" for the motor system; neural firing rate is the dependent variable, or observed response of the system, even though MI activity is widely assumed to generate movement. Despite this false stimulus response reversal, the method has provided a useful construct to study encoding. First, sampling a large portion of the relevant position and velocity space at several different, RMS hand-speed regimes provides a broader sample of the system's behavior under many different, experimenter-controlled conditions. Second, by varying velocity and position independently, the contribution of each of these parameters to MI firing can be examined as separate variables devoid of underlying correlations present in other tasks. Third, the task creates reasonable stationarity in the data. Therefore each spike and movement can be treated as samples uniformly drawn from a stochastic process. Tasks in which trials are divided into epochs for statistical comparisons can violate stationarity because firing rates can show rapid changes (see FIG. 1). The analysis of temporal tuning features as well as frequency domain analysis requires stationarity. The design provides a continuous temporal anchor point ($\tau$), so that the change in spatial encoding for a particular position or velocity variable can be evaluated across time. Time dependent properties are masked in spike triggered averages or histograms when the behavior contains multiple correlated behavioral variables as occurs in step tracking tasks. Finally, the task design in conjunction with multielectrode recording allows us to test the ability to reconstruct any future pseudorandom trajectory based on the data obtained from the firing of several simultaneously recorded neurons during the course of a single trial. Prior work has typically relied on averaging data across trials to reconstruct the location of fixed targets.

MI Tuning Functions

Most neurons showed spatial and temporal structure for both velocity, $N(\vec{v}, \tau)$, and position, $N(\vec{p}, \tau)$. This spatiotemporal tuning was quite heterogeneous; tuning properties varied along a spectrum and did not form into discrete classes, but formed a continuum. The majority of the velocity tuned neurons showed a directional dependence fit by a cosine, consistent with many previous reports using a directional task (Georgopoulos, A. P., Lurito, J. T., Petrides, M., Schwartz, A. B. & Massey, J. T. Mental rotation of the neuronal populaiton vector. Science 243, 234-236 1989; Maynard, E. M., Hatsopoulos, N. G., Ojakangas, C. L., Acuna, B. D., Sanes, J. N., Normann, R. A. & Donoghue, J. P. Neuronal interactions improve cortical population coding of movement direction. Journal of Neuroscience 19, 8083-809. 1999). These neurons also showed a linear dependence on speed also in agreement with other studies (Moran, D. W. & Schwartz, A. B. Motor cortical representation of speed and direction during reaching. Journal of Neurophysiology 82, 2676-2692 1999; indirectly shown in Fu, Q. G., Flament, D., Coltz, J. D. & Ebner, T. J. Temporal encoding of movement kinematics in the discharge of primate primary motor and premotor neurons. Journal of Neurophysiology 73, 836-854 1995). These results show that these features persist in MI despite marked differences in the nature of the tasks performed. Our results also show that speed scales the directional tuning curve without affecting its shape and that firing can be positively or negatively related to speed. Velocity and position encoding neurons are commingled even within the small volume of cortex we examined. In the temporal domain, the phase of directional tuning largely is preserved throughout time, indicating that directional tuning is stably encoded for individual neurons.

Position was best fit by a linear (planar) function suggesting that they act like a gain field (Salinas E, Abbott L F. Coordinate transformations in the visual system: how to generate gain fields and what to compute with them. Prog Brain Res. 2001;130:175-90), but some appeared to have additional structure. Georgopoulos et al. (1984) showed similar planar tuning curves when the position of the hand was held statically in eight target locations arranged radially about the center of the workspace. The results presented herein complement those findings by showing that planar fields apply during hand motion and they provide more local detail about the tuning structure because the space is much more densely sampled than in prior studies. In both cases, the planar model may have fit data because position space has been rather sparsely sampled. Mathematically, a plane will provide a good fit to any two variables on a sufficiently local scale (Taylor's theorem), but planar models of position tuning may not hold on a more global scale. These results imply that single MI neurons do not encode a particular hand position the way that hippocampal neurons encode the spatial location. (Brown, E. N., Frank, L. M., Tang, D., Quirk, M. C. & Wilson, M. A. A statistical paradigm for neural spike train decoding applied to position prediction from ensemble firing patterns of rat hippocampal place cells. Journal of Neuroscience 18, 7411-7425 1998). Instead, as with velocity, there is a preferred direction along which the position maximally scales the firing rate of the neuron. Position planes are heterogeneous in their form and direction. Position space appears to be fully covered by neurons within a small patch of cortex. The completeness of representation is essential to reconstruct position accurately from a limited sample of neurons. Whether some non-planar structure exists may be better revealed if a larger space was sampled and if larger data sets are attained to reduce noise. In other systems, gain fields can become nonlinear when saturated. The role of a position gain field is not known, but the gain structure has been shown in modeling studies to facilitate responses to the strongest among multiple inputs (Salinas and Abbott, 2001). In a polar system, the shape of the tuning functions for position were similar to those for velocity; for example, many cells of both types are sinusoidally tuned for $\theta$ and linearly tuned for $\rho$. A simple model (equation 6) was proposed to describe this shape. Georgopoulos et al. (1984) fit a planar model equivalent to equation (6) to the tuning surfaces for position in a static hold task. However, the tracking task provides a more even and densely sampled distribution of kinematic data than prior tasks in a dynamic situation. These results argue that similar position information is both available in the stationary limb and during tracking motions.

Most noteworthy are the cells in which position and velocity appeared to be independently coded variables. For some velocity tuned cells, position tuning could be explained solely as a consequence of these cells' strong velocity tuning. However, for other cells, the position tuning was not an obvious function of velocity, suggesting that these variables are independently encoded, in some cases by separate populations of neurons. Position cells invariant to velocity would seem to be useful to provide a movement independent representation of hand location in space, even while the hand is in motion. Such invariance related computations may require large numbers of neurons. (Salinas and Abbott, 2001), but the ease with which hand motion related neurons were detected suggests that very large populations are engaged during tracking. Whether these neurons encode position uniquely, or combine other inputs (e.g. acceleration, amplitude) not measured in the data presented herein has not been established.

Salinas and Abbott (2001) suggest heterogeneous mixes of cells with these sorts of encodings, which is suited to translation invariant representations. In the motor cortex, this could mean that ensembles of neurons could represent particular kinds of movements irrespective of their particular location in space. Such a network might also account for motor equivalence were the same action is produced, with greater structural similarity, from multiple effectors. Interestingly, formation of these kinds of networks seems to require Hebbian like learning; the horizontal connections of motor cortex show exactly this type of synaptic strength change when new motor tasks are learned (Rioult-Pedotti M S, Friedman D, Hess G, Donoghue J P. Strengthening of horizontal cortical connections following skill learning. Nat Neurosci. July, 1998;1 (3):230-4). Distributed, multiple representation with gain fields is also thought to be well-suited to provide signals that can be readily decoded by their target structures (Salinas and Abbott, 2001). In other regions of cortex, attention or gaze angle act as gain modulators, while in MI position and speed both appear to engage this mechanism; more indirect evidence suggest that gaze may also influence MI neurons (Baker J T, Donoghue J P, Sanes J N. Gaze direction modulates finger movement activation patterns in human cerebral cortex. J Neurosci. Nov. 15, 1999;19(22):10044-52). Thus, MI may be involved in the coordinate transform similar to that modeled by Zipser and Anderson (Zipser D, Andersen R A. A back-propagation programmed network that simulates response properties of a subset of posterior parietal neurons. Nature. Feb. 5, 1988;331(6158):679-84) ranging from abstract plans of hand trajectory to the more direct command of the effector. The observation that hand trajectory can be so well recovered from MI, also suggests that it lies at an interface of planning and performance of visually guided tracking movements.

Thus, MI tuning functions are heterogeneous in position and velocity encoding; the evidence presented herein does not support the idea that position and velocity neurons form separate classes, but rather we suggest that encoding of these variables is represented across a continuum in which one or the other is differently weighted. These results show that these cells are intermingled within a small volume of cortex (the ~2×2 mm region we record) and that this diverse population is active during tracking motions.

Motor spatiotemporal receptive fields can be compared to spatio-temporal visual receptive (DeAngelis, G. C., Ghose, G. M., Ohzawa, I. & Freeman, R. D. Functional micro-organization of primary visual cortex: receptive field analysis of nearby neurons. Journal of Neuroscience 19, 4046-4064. 1999), or spectro-temporal auditory fields(Kowalski, N., Depireux, D. A. & Shamma, S. A. Analysis of dynamic spectra in ferret primary auditory cortex. Journal of Neurophysiology 76 350. 1996) that have been described using a similar systems approach. Tuning function is meant to be a more neutral term because what is actually encoded by the neuron has not been established (see below). These analyses have revealed a similar diversity in tuning functions when considered across the temporal and spatial domain (Deangelis et al., 1999). However, the motor functions describe herein are much broader than sensory fields, but this comparison is complicated by the much longer auto correlation times of movement 'stimuli', making them appear to change much more slowly than sensory fields. There is no obvious way to rescale these differences, so that temporal comparisons between sensory motor fields, except for their peak time, must be cautiously applied.

Temporal Information About Position and Velocity

Tracking temporal tuning profiles revealed that MI neurons nearly continuously provided information about position and velocity. While the amount of information was similar the time course of each differed. Further, our parallel recordings show that these temporal differences are part of the natural course of firing during an evolving movement and cannot be attributed to trial-to-trial or animal-to-animal differences that occur with serial recording. The method presented herein lacks linear assumptions of multiple linear regression models which have demonstrated that single MI neurons carry information about average hand direction, velocity, position and acceleration (Ashe, J. & Georgopoulos, A. Movement parameters and neural activity in motor cortex and area 5. Cerebral Cortex 4, 590-600. 1994; Fu et al. 1995) Nevertheless these results are consistent with those found here, these results extend these findings to show that relatively detailed position and velocity information occurs throughout tracking, not just in the average across trials. All studies appear to agree that velocity tuning is a dominant feature of MI neurons. Ashe and Georgopoulos (1994) regression analysis demonstrated that 27% of cells predominantly tuned to velocity as opposed to 17% of cells that were primarily position tuned. We find a mix of velocity and position information across cells. The quantitative analysis presented herein reveals, however, that MI cells on average carried 10% more information about velocity than position. Thus, the amount of information available about position and velocity is roughly equal, contrary to what might be expected from emphasis on directional tuning of MI neurons. Information values for instantaneous position or velocity measured during performance of this tracking task were small compared to those previously computed for static target direction TD in the center-out task (Hatsopoulos, N. H., Ojakangas C. L., Paninski L. & Donoghue J. P. Information about movement direction obtained from synchronous activity of motor cortical neurons. Proceedings of the National Academy of Sciences U.S.A. 95, 15706-15711 1998). Information rates derived from FIG. 16A appear to reach a maximum of about 1 bit/sec, which is up to 100 times lower than has been reported for the amount of information in the spike trains of neurons in sensory cortex (Rieke, F., Warland, D., de Ruyter van Steveninck, R. & Bialek, W. Spikes: Exploring the Neural Code. MIT Press, Cambridge, Mass. 1997).

Firing rate appears to vary smoothly as a function of these parameters, and the conditional distributions of the signal given spike count depend only weakly on the spike count (FIG. 11). Our results are in agreement with previous results, including those of Ashe and Georgopoulos, 1994, where analysis of variance techniques performed on radial task data indicate that (static) target direction accounted for much more of the variance in firing rate than did time-varying hand position, velocity, or acceleration. However, it was found that the information content of MI cells for velocity was only 10% greater, on average, than the information content for position (FIG. 13), whereas Ashe and Georgopoulos, 1994, found a much stronger preference for hand velocity than position. These discrepancies may be due either to the statistical differences between the tracking and center-out paradigms (such as the strong dependence between target direction, hand position, and velocity demonstrated in FIG. 1B), or to differences between the (linear) analysis of variance procedure employed in Ashe and Georgopoulos and the (nonlinear) information-theoretic analysis employed here.

The data presented herein suggest that position and velocity information is specified over quite different time scales. Velocity is tightly peaked with a lead of about ~100 ms. Using serial, single cell recordings, Ashe and Georgopoulos (1994) found that their linear model could account for the largest percentage of the variance when the firing rate led the kinematics by 90 ms and Fu et al. (1995) found that target direction on average accounted for the firing rate ~115 ms prior to movement onset using an analysis of variance. Together, these data suggest that MI firing specifies velocity just before it is achieved. Unlike velocity, we showed that position information is temporally dispersed, with peaks occurring both before and after Tau. The pattern generated by a group of simultaneously recorded neurons demonstrates that position information is continuously available to MI neurons; both after movements are executed as well as when they are being prepared.

Figure 13:
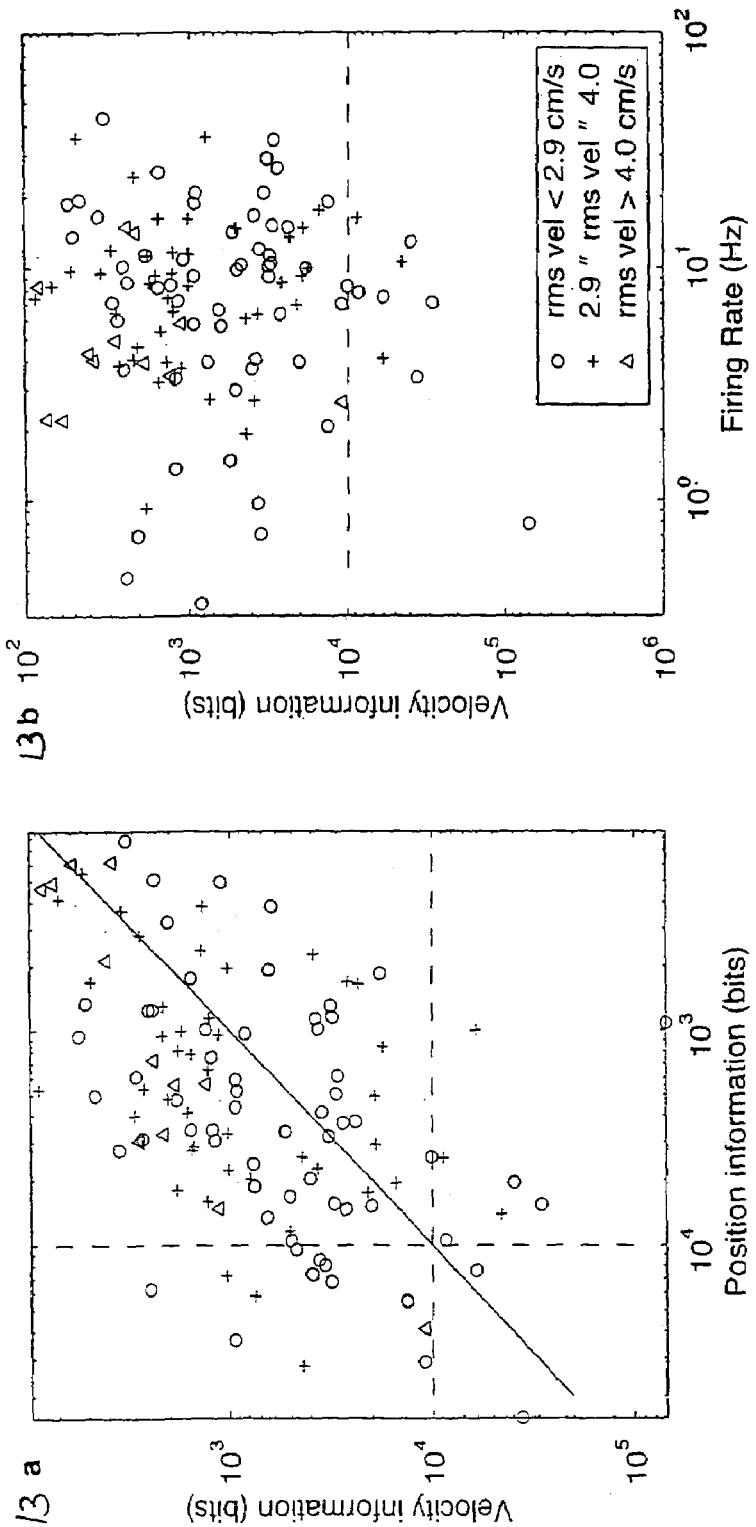
FIGS. 13A-13B summarize the distribution of information values for velocity and position of MI cells.

The time course of velocity and position tuning of these temporal tuning curves varied considerably and these differences cannot be explained in terms of kinematic or motivational differences between experiments, which could have explained heterogeneity observed in earlier work (Kakei, S., Hoffmnan, D. S. & Strick, P. L. Muscle and movement representations in the primary motor cortex. Science 285, 2136-2139 1999; Porter, R. & Lemon, R. Corticospinal function and voluntary movement. Clarendon Press, Oxford 1993). Information tuning curves were heterogeneous not just in their shape but also in their amplitude (FIG. 13). Information content for hand velocity and position varied over two orders of magnitude and did not depend on the mean firing rate or variance. This result is consistent with the conclusion that these are fundamental variables encoded in these neurons. However, this hypothesis would require further demonstration that information content is not dependent on limb dynamics (Kalaska, J. F., Cohen, D. A. D., Hyde, M. L. & Prudhomme, M. A comparison of movement direction-related versus load direction-related activity in primate motor cortex, using a two-dimensional reaching task. Journal of Neuroscience 9, 2080-2102; 1989) or other kinematic variables such as arm posture (Scott, S. H. & Kalaska, J. F. Reaching movements with similar hand paths but different arm orientations. I. Activity of individual cells in motor cortex. Journal of Neurophysiology 77, 826-52 1997).

Neurons in MI fire at low rates during visually guided tracking and firing rate modulations typical of step tracking tasks are not readily evident. Information theoretic analysis provided a quantitative and comparative measure of position and velocity information encoded. Across the population, MI encodes similar amounts of position and velocity information, with each ranging over two orders of magnitude. The information values observed here, which peak at 0.01 bits are substantially smaller than 0.33 bits (calculated in 50 ms bins) related to static target direction in the center-out task, even when corrected for differences in the bin size used to calculate information (Hatsopoulos et al., '98). The velocity and position information content per neuron is broadly dispersed and only weakly correlated (FIG. 13) suggesting a considerable heterogeneity in the population of neurons. Although difficult to compare directly, the information conveyed by firing during tracking seems relatively small compared to that seen for force steps in single joint actions (Humphrey, D. R., Schmidt, E. M. & Thompson, W. D. Predicting measures of motor performance from multiple cortical spike trains. Science 170, 758-762 1970), where there is a strong firing correlation with the time derivative or force or step movements to targets (Hatsopoulos et al., '98, Ashe and Georgopoulos, '94) where there are very large firing modulations that correlate with velocity. However, the signal reconstruction presented herein demonstrates that small populations of neurons carry sufficient information to return a reasonably good reconstruction of the low frequency components of hand trajectory.

Signal Reconstruction

A linear regression method that was able to recover hand trajectory from the firing of MI neurons was developed. This decoding verifies that useful position and velocity information, described by spatiotemporal tuning functions, exists in a usable form. The results presented herein demonstrate that a simple linear decoding algorithm, given the firing patterns of small, randomly chosen set of neurons and their prior firing patterns over time, can reconstruct any future hand trajectory through two-dimensional space (FIG. 14, Table 1). Neurons were randomly chosen in the sense that no pre-selection of well-tuned neurons was performed; all well-isolated units which happened to be within the recording range of our chronically-implanted electrode array during a given experiment were analyzed. Moreover, relatively small sub-populations of cells can capture significant fractions of the available information to allow reasonable reconstruction of hand trajectory (FIG. 15B). The ability to reconstruct trajectory using a simple algorithm from small sets of neurons suggests that is would be relatively straightforward to control devices in complex ways using limited neural samples from MI (Kennedy, P. R. & Bakay, R. A. Restoration of neural output from a paralyzed patient by a direct brain connection. Neuroreport 9, 1707-11998; Kennedy, P. R. & Bakay, R. A. Restoration of neural output from a paralyzed patient by a direct brain connection. Neuroreport 9, 1707-1; Wessberg, J., et al. Real-time prediction of hand trajectory by ensembles of cortical neurons in primates. Nature 408, 361-365 2000) and the decoding approach presented herein. Such neural prosthetics could be used to restore movement to paralyzed individuals.

Previous attempts to infer motor behavior from neural population activity include the "population vector" approach pioneered by Georgopoulos and adopted by many others (Georgopoulos et al., '82, Moran and Schwartz, '99; Kalaska et al.). There are several essential differences between the population vector approach and linear reconstruction as applied here. First, the PV method estimates only the average direction of motion of the hand, to one of eight radially located targets, denoted TD (see FIG. 1) and typically does not attempt to reconstruct the hand position as a time-varying signal. TD is an estimated static, discrete quantity. Second, the reconstruction presented herein uses the neurons detailed the spatiotemporal tuning functions $N(\vec{v}, \tau)$ or $N(\vec{p}, \tau)$, where previous studies use only a given cell's PD, defined as the peak of the cell's tuning curve as a function of target direction. Third, the PV method assumes that the firing rates of two given neurons are conditionally independent, which is mandatory when two cells are recorded separately, but has been shown to be false for simultaneously active populations (Maynard, E. M., Hatsopoulos, N. G., Ojakangas, C. L., Acuna, B. D., Sanes, J. N., Normann, R. A. & Donoghue, J. P. Neuronal interactions improve cortical population coding of movement direction. Journal of Neuroscience 19, 8083-809. 1999). Fourth, the approach taken here assumes no model of the firing process while the PV method uses an explicit cosine model of firing; this assumption is not necessary. The actual firing pattern of a cell serves well as a model of future information.

The PV approach also successfully reconstructs the spatial aspects of the hand path in various drawing tasks (Schwartz, A. Motor cortical activity during drawing movements: population representation during sinusoid tracing. Journal of Neurophysiology 70:28-36. 1993; Moran, D. W. & Schwartz, A. B. Motor cortical activity during drawing movements: population representation during spiral tracing. Journal of Neurophysiology 82, 2693-270 1999). These reconstructions are based on using these "center-out" PD's to reconstruct a curve (e.g., a sinusoid in Schwartz, '93, or a spiral in Moran and Schwartz, '99) that a monkey had traced out on a touch screen. However, the temporal details were obscured by averaging over trials, so that only spatial, not temporal, information about the path is recovered from a population of selected neurons (need for uniform distribution, etc). By contrast, it is shown here that observation of ~20 min of neural firing can produce a set of temporal filters sufficient to reconstruct future hand trajectories based on the firing of that population. This reaffirms that considerable information about the time varying path of the hand is available from linear combinations of firing of simultaneously active MI neurons.

Humphrey et al. (Humphrey, D. R., Schmidt, E. M. & Thompson, W. D. Predicting measures of motor performance from multiple cortical spike trains. Science 170, 758-762 1970) and Wessberg et al. (Wessberg et al., 2000) in motor cortex and (Brown et al., 1998) for hippocampal place cells have employed similar reconstruction methods. Humphrey et al. recorded simultaneously from up to eight MI neurons and used time-domain linear regression techniques similar to those described here to estimate various single joint-related behavioral parameters; this method also works well for multijoint movements. More recently, Wessberg et al. (Wessberg et al., 2000) obtained similar results, using one task in which the hand was constrained to move along a one-dimensional track and another in which the monkey reached repetitively for a piece of food. Our work is the first in which random multidimensional movements were reconstructed. These linear methods are weak in several regards There is a great deal of variability across experiments (Table 1), some of which can be at least partially accounted for by differences in the time the cells were observed and in the total number of cells observed (see FIGS. 15B herein and Wessberg et al.'s FIGS. 2e-f and 3f-g; note that they plotted r in these figures, not $r^2$ as here). However, even in these (or Wessberg et al.'s) experiments, it was not possible to account for all of the available variance. In addition, the linear technique fails to capture effectively all of the variance above 0.5 Hz. Note that this does not rule out the hypothesis that MI cells encode higher-frequency information about other aspects of the kinematic behavior of the arm, including joint angles and muscle activity (see Lemon, R. N. The output map of the primate motor cortex. Trends in Neuroscience 11, 5011-506 1988), for example, for clear examples of higher-frequency EMG information available in cortical spike trains). It should be noted that the results presented herein are slightly inconsistent with those of Wessberg et al. (Wessberg et al., 1900), who show significant coherence between neural activity and hand position at higher frequencies in their FIG. 2(a-b), but it is possible that simple statistical considerations can account for these discrepancies.

Neural activity during tracking was qualitatively different from that found in previous studies in step tracking tasks. In the continuous tracking task, MI neurons showed low mean firing rates and few rapid rate modulations. This was not a feature of the cells selected. Rate modulations typical of MI neurons were evident in the same cells when these monkeys performed interleaved step tracking trials. Thus, these results show that MI contributes to motions of the hand directed under visual guidance, and, under these conditions they operate in a low firing rate regime. Our linear reconstruction and information theoretic analyses unequivocally demonstrate that in this regime neurons are fully capable of encoding hand trajectory and that this coding is unrelated to global variations in behavior. Further, the amount of information encoded is not related to the mean firing rate, so that similar amounts of information about hand motion may be encoded in the modulations of cells with low and high firing rates. The present task may be compared to the closed loop oculomotor pursuit system. Unlike that system the same sets of cortical neurons seem to be engaged in both ballistic and continuous tracking movements, although this dichotomy may be artificial in the skeletomotor system. These data suggest that the information encoded is an intrinsic feature of the firing rate process in MI neurons. Our data also show that neurons are broadly tuned for position and velocity because firing rate varies slowly as a function of these variables, as can be seen in the tuning function plots of FIGS. 8 and 9.

What is Coded in MI?

The results presented herein demonstrate that information about hand trajectory exists in the firing rate of MI neurons, but it does not demonstrate that these neurons actually encode this variable, nor does it mean that downstream structures decode this information. Hand trajectory is correlated with other variables, including joint angles, torques, (Todorov, E. Direct cortical control of muscle activation in voluntary arm movements: a model. Nature Neuroscience 3, 391-39. 2000; Fetz, E. E. & Finocchio, D. V. Operant conditioning of specific patterns of neural and muscular activity. Science 174, 431 1980; Mussa-Ivaldi, F. A. Do neurons in the motor cortex encode movement direction? An alternative hypothesis. Neuroscience Letters 91, 106-11. 1988; Todorov, 2000). It would be ideal to uncouple each of these variables to determine which is best coded. The tracking task makes it possible to derive information curves for these other behavioral signals, so that both the quantity and time course can be measured with a unit that can be directly compared across variables. Nevertheless, our quantitative findings place strong constraints on the variables that are encoded in Ml firing (Pugh, M., Ringach, D., Shapley, R. & Shelley, M. Computational Modeling of Orientation Tuning Dynamics in Monkey Primary Visual Cortex. Journal of Computational Neuroscience 8, 143-15. 2000). These signal reconstruction methods show that trajectory information can be recovered from Ml firing and that this information is improved when longer times or more neurons are considered, but does not address any readout mechanism. However, it is shown that during tracking there is a continual flow of information that is undoubtedly passed to large numbers of neurons which are capable of integrating across populations. Finally, these results speak to the issue of functional organization of Ml. These results show that a small group of randomly selected neurons within a 2×2 mm cortical region, which represents approximately 4% of the 10×10 mm Ml arm area, contain nearly a full representation of all velocities and positions. This argues for a highly distributed representation of information within Ml, any part of which appears capable of computing hand trajectory.

Immediate, Real-Time Use of a Neurally-Based Control Signal for Movement

An example of an application of the neurological signal decoding methods described above is the use of these signals to drive an artificial device. The activity of motor cortex (MI) neurons predicts movement intent-sufficiently well to be used as a control signal to drive simple movements in artificial devices. However, use of this signal has required significant training and achieves a limited movement repertoire. Here it was demonstrated how activity from a small numbers of MI neurons can be decoded into a signal that a monkey can immediately use to move a computer cursor to any new position in its workspace. These results, based upon recordings made by an electrode array suitable for human use, suggest that neurally based control is feasible in paralyzed humans.

Recordings of multiple MI neurons were obtained from three *Macaca mulatta* monkeys implanted with an Utah Intracortical Multielectrode Array. Monkeys used their hand to move a manipulandum that controlled the position of a cursor on a video monitor to reach visually displayed targets. Monkeys tracked a continuously moving target that followed a psuedorandom trajectory. A linear filter method was used to test whether we could reliably reconstruct hand trajectory from neural activity obtained on subsequent trials. Reconstructions accurately reflected hand trajectory, they accounted for over 60% of the variance present in actual hand motion ($r^2 > 0.6$).

One of these monkeys then performed a closed-loop version of the experiment, in which reconstructions were computed continuously online in real-time. Here, an average of 1 minute of tracking and recording was used to build a preliminary linear filter model. Once this model was constructed, the task was switched to require movement to stationary targets. In this case the cursor movement was driven by the filtered neural data. For an additional average period of 2 minutes, new filters were constructed.

The monkey immediately used this neural-activity based signal, without any further training, to acquire stationary targets (0.18 degrees visual angle) displayed one at a time at random locations on the monitor. The time required to acquire targets using this signal was only slightly greater than using actual hand position (FIG. 1). The difference between the time lags due to actual hand and reconstruction control were not significant at alpha=0.05 by the one-sided Kolgorov-Smirnov test. Target acquisition was unsuccessful (it was not achieved within 1 minute) if filters were randomly shuffled amongst cells or if a random number was added to the filter coefficients, indicating that properly constructed filters are necessary for the animal to acquire functional control over the prediction signal.

Neuroprosthetic systems may comprise two learning systems: a mathematical algorithm, and the subject's brain. The primary role of the former is to transform neural activity into a control signal that exists in a functionally usable regime. Visual and other feedback coupled with a subject's dynamic learning can compensate for inaccuracies in the model to provide an easily and voluntarily controlled signal. Our results demonstrate that a simple mathematical approach, coupled with a biological system, provides effective decoding necessary for useful brain machine interfaces that can aid neurologically impaired humans.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for controlling a device comprising:
   providing a sensor sensing electrical activity of a plurality of neurons over time;
   generating a neural control vector by storing the sensed electrical activity of the plurality of neurons at each of successive time bins;
   providing a control filter;
   calculating an innerproduct between the neural control vector and the control filter to provide a control variable; and
   controlling an output device with the control variable.

2. The method of claim 1 wherein the sensor comprises an array of electrical sensing elements, and the neural control vector represents the sensed electrical activity at each of the electrical sensing elements at each of the successive time bins.

3. The method of claim 1 wherein the control filter for calculation of a control variable provides a least mean square error between an output of the output device and an intended output.

4. The method of claim 1 wherein the electrical activity of neurons is sensed over 1 to 1000 time bins.

5. The method of claim 1 wherein each of the time bins is 1 to 1000 ms.

6. The method of claim 1 wherein an application of the neural control vector to the control filter results in an innerproduct.

7. The method of claim 1 wherein providing a control filter comprises generating a control filter based on a previously sensed electrical activity and kinematic data concurrently recorded with the previously sensed electrical activity.

8. A method of generating a control filter comprising:
   providing a sensor sensing electrical activity of a plurality of neurons over time;
   generating a neural control vector by storing the sensed electrical activity of the plurality of neurons at each of successive time bins;
   calculating filter coefficients which when applied to the neural control vector reconstructs motor control parameters.

9. The method of claim 8 further comprising calibration by tracking a stimulus moving through a motor workspace in at least one spatial dimension.

10. The method of claim 9 further comprising calibration based on a psuedorandom tracking task.

11. The method of claim 8 further comprising calibration whereby a user acquires stationary and moving targets in at least one spatial dimension using a neural control signal with previously generated filters and neural and kinematic data concurrent with the target acquisition to build new filters.

12. The method of claim 8 wherein the sensor comprises an array of electrical sensing elements, and the neural control vector represents the sensed electrical activity at each of the electrical sensing elements at each of the successive time bins.

* * * * *